US012304893B2

(12) United States Patent
Chen et al.

(10) Patent No.: US 12,304,893 B2
(45) Date of Patent: *May 20, 2025

(54) PROCESS FOR SYNTHESIS OF 2-AMINO-5-CHLORO-N-,3-DIMETHYLBENZAMIDE

(71) Applicants: FMC Corporation, Philadelphia, PA (US); FMC Agro Singapore Pte. Ltd., Singapore (SG)

(72) Inventors: Liang Chen, Shanghai (CN); Yefeng Fan, Shanghai (CN); Jianhua Mao, Shanghai (CN); Zhijian Xu, Shanghai (CN)

(73) Assignees: FMC CORPORATION, Philadelphia, PA (US); FMC IP TECHNOLOGY GMBH, Neuhausen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/070,827

(22) Filed: Nov. 29, 2022

(65) Prior Publication Data

US 2023/0096826 A1 Mar. 30, 2023

Related U.S. Application Data

(60) Division of application No. 17/721,781, filed on Apr. 15, 2022, now Pat. No. 11,542,241, which is a continuation of application No. PCT/US2020/057726, filed on Oct. 28, 2020.

(60) Provisional application No. 62/929,138, filed on Nov. 1, 2019.

(51) Int. Cl.
 C07C 237/30 (2006.01)
 C07C 231/14 (2006.01)
 C07C 237/28 (2006.01)
 C07D 209/38 (2006.01)
 C07D 265/26 (2006.01)

(52) U.S. Cl.
 CPC .......... *C07D 265/26* (2013.01); *C07C 231/14* (2013.01); *C07C 237/28* (2013.01); *C07D 209/38* (2013.01)

(58) Field of Classification Search
 CPC .................................................. C07C 237/30
 See application file for complete search history.

(56) References Cited

U.S. PATENT DOCUMENTS 9,499,495 B2   11/2016   Thompson et al.
11,542,241 B2 *  1/2023   Chen .................... C07D 209/38

FOREIGN PATENT DOCUMENTS

CN  103058993 A   4/2013
CN  103058993 B   6/2014
JP  2002541134 A  12/2002
JP  2008523069 A   7/2008
WO     0058288 A1  10/2000
WO     0059868 A1  10/2000
WO  2005033112 A2   4/2005
WO  2006062978 A1   6/2006
WO  2008010897 A2   1/2008
WO  WO-2009143049 A1 * 11/2009 ........... C07D 239/90

OTHER PUBLICATIONS

Joaquim F. M. Da Silva et al, "The Chemistry of Isatins: a Review from 1975 to 1999," J. Braz. Chem. Soc., vol. 12, No. 3, 273-324, 2001.
Frank D. Popp, "The Chemistry of Isatin," Advances in Heterocyclic Chemistry, Academic Press, vol. 18, 1975, pp. 1-58.
International Search Report and Written Opinion for corresponding PCT/US20/57726 mailed Jan. 11, 2021, 13 Pages.
Rati K. P. Tripathi et al, "Discovery of 3-Hydroxy-3-phenacyloxindole Analogues of Isatin as Potential Monoamine Oxidase Inhibitors", ChemMedChem,vol. 11, No. 1, Nov. 23, 2015.
Malinowski Zbigniew et al, "Synthesis and biological evaluation of some amino- and sulfanyl-3H-quinazolin-4-one derivatives as potential anticancer agents", Jun. 26, 2015.
Shyam Panga et al, "Synthesis and Ameliorative Effect of Isatin-Mesalamine Conjugates on Acetic Acid-induced Colitis in Rats", Journal of Heterocyclic Chemistry,vol. 56, No. 3, Feb. 7, 2019.
Yang Li et al, "Thioxo-dihydroquinazolin-one Compounds as Novel Inhibitors of Myeloperoxidase", ACS Medicinal Chemistry Letters,vol. 6, No. 10, Aug. 31, 2015.
Wang Yu-Wei et al, "Oxidative ring-opening of isatins for the synthesis of 2-aminobenzamides and 2-aminobenzoates", Tetrahedron,vol. 75, No. 11, Feb. 6, 2019.
Vittoria Colottaa et al, "Glycine-NMDA Antagonists Synthesis and Biological Evaluation of a Series of Quinazoline-2-carboxylic Acids and Quinazoline-2,4-diones as Glycine-NMDA Antagonists: A Pharmacophore Model Based Approach", Archiv Der Pharmazie,vol. 330, No. 5, 1997, p. 129-134.
Maha Y. Jarrah and Viktor Thaller, "300 Mhz 1NMR spectra of indolo[2,1-b]quinazoline-6, 12-dione, tryptanthrine and its 2- and 8-chloro derivatives", Journal of Chemical Research, Miniprint, vol. 6, pp. 2601-2609, 1980.
Marvel et al, "Isatin". Organic Syntheses, Coll. vol. 5, 1925.
Reissenweber et al, "Oxidation von Isatinen zu 7-Isatosaureanhydriden und 2,3-Dioxo-1,4-benzoxazinen", Angewandte Chemie, vol. 92, No. 3, 1980, pp. 196-197. Appended with English translation.
Tojo et al, "Quinoline-3-carbothioamides and Related Compounds as Novel Immunomodulating Agents", Biorganic & Medicinal Chemistry Letters, vol. 12, 2002, pp. 2427-2430.
Aneja et al, "Design and development of 9-Isatin-triazole hydrazones as potential inhibitors of microtubule affinity-regulating kinase 4 for the therapeutic management of cell proliferation and metastasis", European Journal of Medicinal Chemistry, vol. 163, 2019, pp. 840-852.
Silva et al, "Chlorination of Isatins with Trichloroisocyanuric Acid", J. Braz. Chem. Soc., vol. 22, No. 2, 2011, 257-263.

(Continued)

*Primary Examiner* — John S Kenyon
(74) *Attorney, Agent, or Firm* — Armstrong Teasdale LLP

(57) ABSTRACT

Described herein are novel methods of synthesizing 2-amino-5-chloro-N,3-dimethylbenzamide. Compounds prepared by the methods disclosed herein are useful for preparation of certain anthranilamide compounds that are of interest as insecticides, such as, for example, the insecticides chlorantraniliprole and cyantraniliprole.

17 Claims, No Drawings

(56) References Cited

OTHER PUBLICATIONS

Synthesis and biological evaluation of some amino- and sulfanyl-3H-quinazolin-4-one derivatives as potential anticancer agents, Z.Malinowski et al.
ctd. Monatsh Chem, 146(2015), 1723-1731, DOI: 10.1007/s00706-015-1508-6.
Discovery of Tryptanthrin Derivatives as Potent Inhibitors of Indoleamine 2,3-Dioxygenase with Therapeutic Activity in Lewis Lung Cancer (LLC) Tumor-Bearing Mice.
ctd. S. Yang et al., J. Med. Chem., 56(2013), 8321-8331, DOI: 10.1021/jm401195n.
Search report from office action for Japanese application No. 2022-500859 mailed on Feb. 22, 2024.
Yang et al., "Discovery of Tryptanthrin Derivatives as Potent Inhibitors of Indoleamine 2,3-Dioxygenase with Therapeutic Activity in LLC tumor-bearing Mice", Journal of Medicinal Chemistry, 2013, pp. 8321-8331, 56(21).

* cited by examiner

PROCESS FOR SYNTHESIS OF 2-AMINO-5-CHLORO-N-,3-DIMETHYLBENZAMIDE

CROSS-REFERENCE TO RELATED APPLICATION

This application is a U.S. Divisional application of U.S. patent application Ser. No. 17/721,781, filed Apr. 15, 2022, which is a bypass U.S. Continuation application of International Patent Application No. PCT/US2020/057726, filed Oct. 28, 2020, which claims priority to U.S. Provisional Application No. 62/929,138, filed Nov. 1, 2019, each of which is hereby incorporated by reference herein.

FIELD OF INVENTION

This disclosure is directed to novel methods of synthesizing 2-amino-5-chloro-N,3-dimethylbenzamide. Compounds prepared by the methods disclosed herein are useful for preparation of certain anthranilamide compounds that are of interest as insecticides, such as, for example, the insecticides chlorantraniliprole and cyantraniliprole.

BACKGROUND

Conventional processes for the production of 2-amino-5-chloro-N,3-dimethylbenzamide are subject to several industrial concerns, such as hazardous materials, high cost, relatively long method steps, and complicated operations.

The present disclosure provides novel methods useful for preparing 2-amino-5-chloro-N,3-dimethylbenzamide and derivatives thereof. The benefits of the methods of the present disclosure compared to previous methods are numerous and include reduced cost, eliminated need for mixed solvent separations, reduced waste, relatively short method steps, simplified operation complexity, and reduced process hazards.

BRIEF DESCRIPTION

In one aspect, provided herein is a method of preparing a compound of Formula VI, wherein

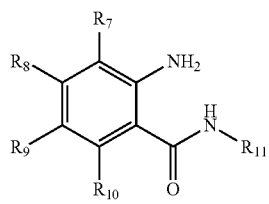

(Formula VI)

each of $R_7$-$R_{10}$ is independently selected from hydrogen, halogen, halogenated $C_1$-$C_5$ alkyl, and $C_1$-$C_5$ alkyl;

wherein at least one of $R_7$-$R_{10}$ is a halogen; and wherein $R_{11}$ is selected from branched $C_1$-$C_{10}$ alkyl and unbranched $C_1$-$C_{10}$ alkyl, the method comprising I) forming a mixture comprising
  A) a compound of Formula V, wherein

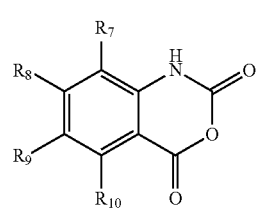

(Formula V)

each of $R_7$-$R_{10}$ is independently selected from hydrogen, halogen, halogenated $C_1$-$C_5$ alkyl, and $C_1$-$C_5$ alkyl;

wherein at least one of $R_7$-$R_{10}$ is a halogen; and wherein the compound of Formula V is prepared according to a method comprising
  i) forming a first mixture comprising
    a) a compound of Formula III, wherein

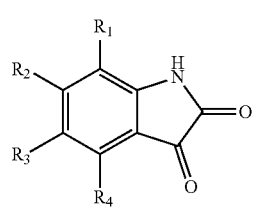

(Formula III)

each of $R_1$-$R_4$ is independently selected from hydrogen, halogen, and $C_1$-$C_5$ alkyl;
    b) a solvent; and
    c) a halogenation reagent;
  ii) reacting the first mixture;
  iii) introducing a second mixture to the first mixture to form a third mixture, the second mixture comprising
    d) an oxidation agent; and
    e) a catalyst; and
  iv) reacting the third mixture;
  B) an alkylamine; and
  C) a solvent; and
II) reacting the mixture.

In one aspect, provided herein is a method of preparing a compound of Formula V, wherein

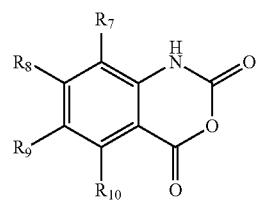

(Formula V)

each of $R_7$-$R_{10}$ is independently selected from hydrogen, halogen, halogenated $C_1$-$C_5$ alkyl, and $C_1$-$C_5$ alkyl; and wherein at least one of $R_7$-$R_{10}$ is a halogen, the method comprising I) forming a first mixture comprising
   A) a compound of Formula III, wherein

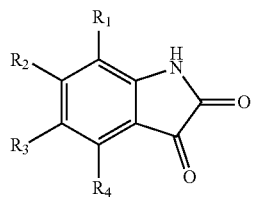

(Formula III)

each of $R_1$-$R_4$ is independently selected from hydrogen, halogen, and $C_1$-$C_5$ alkyl;
   B) a solvent; and
   C) a halogenation reagent;
II) reacting the first mixture;
III) introducing a second mixture to the first mixture to form a third mixture, the second mixture comprising
   D) an oxidation agent; and
   E) a catalyst; and
IV) reacting the third mixture.

In one aspect, provided herein is a method of preparing a compound of Formula VI, wherein

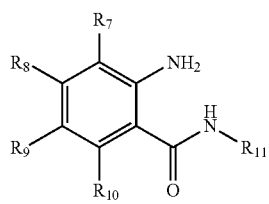

(Formula VI)

each of $R_7$-$R_{10}$ is independently selected from hydrogen, halogen, halogenated $C_1$-$C_5$ alkyl, and $C_1$-$C_5$ alkyl;
wherein at least one of $R_7$-$R_{10}$ is a halogen; and
wherein $R_{11}$ is selected from branched $C_1$-$C_{10}$ alkyl and unbranched $C_1$-$C_{10}$ alkyl, the method comprising
   I) forming a mixture comprising
      A) a compound of Formula V, wherein

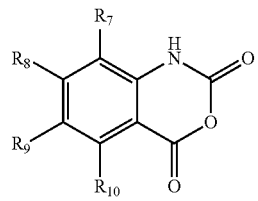

(Formula V)

each of $R_7$-$R_{10}$ is independently selected from hydrogen, halogen, halogenated $C_1$-$C_5$ alkyl, and $C_1$-$C_5$ alkyl;
wherein at least one of $R_7$-$R_{10}$ is a halogen; and
wherein the compound of Formula V is prepared according to a method comprising i) forming a mixture comprising
   a) a compound of Formula IV, wherein

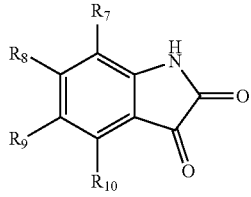

(Formula IV)

each of $R_7$-$R_{10}$ is independently selected from hydrogen, halogen, halogenated $C_1$-$C_5$ alkyl, and $C_1$-$C_5$ alkyl; and
wherein at least one of $R_7$-$R_{10}$ is a halogen;
   b) an oxidation agent;
   c) a solvent; and
   d) a catalyst; and
ii) reacting the mixture;
   B) an alkylamine; and
   C) a solvent; and
II) reacting the mixture.

In one aspect, provided herein is a method of preparing a compound of Formula V, wherein

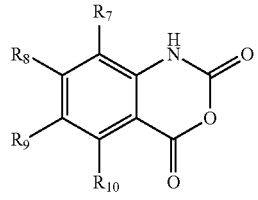

(Formula V)

each of $R_7$-$R_{10}$ is independently selected from hydrogen, halogen, halogenated $C_1$-$C_5$ alkyl, and $C_1$-$C_5$ alkyl; and
wherein at least one of $R_7$-$R_{10}$ is a halogen, the method comprising
   I) forming a mixture comprising
      A) a compound of Formula IV, wherein

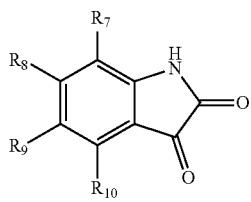

(Formula IV)

each of $R_7$-$R_{10}$ is independently selected from hydrogen, halogen, halogenated $C_1$-$C_5$ alkyl, and $C_1$-$C_5$ alkyl; and
wherein at least one of $R_7$-$R_{10}$ is a halogen;
      B) an oxidation agent;
      C) a solvent; and
      D) a catalyst; and
   II) reacting the mixture.

In one aspect, provided herein is a method of preparing a compound of Formula IV, wherein

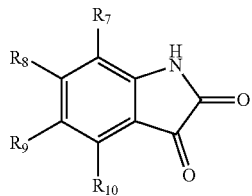
(Formula IV)

each of $R_7$-$R_{10}$ is independently selected from hydrogen, halogen, halogenated $C_1$-$C_5$ alkyl, and $C_1$-$C_5$ alkyl;
wherein at least one of $R_7$-$R_{10}$ is a halogen, the method comprising
  I) forming a mixture comprising
    A) a compound of Formula III, wherein

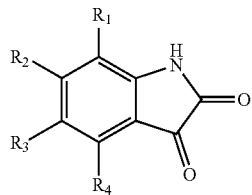
(Formula III)

each of $R_1$-$R_4$ is independently selected from hydrogen, halogen, and $C_1$-$C_5$ alkyl;
  B) a solvent;
  C) a halogenation reagent; and
  II) reacting the mixture.

In one aspect, provided herein is a method of preparing a compound of Formula III, wherein

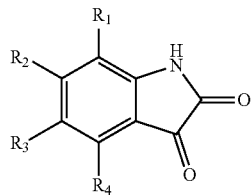
(Formula III)

each of $R_1$-$R_4$ is independently selected from hydrogen, halogen, and $C_1$-$C_5$ alkyl, the method comprising
  I) forming a mixture comprising
    A) a compound of Formula II, wherein

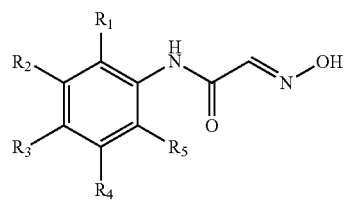
(Formula II)

each of $R_1$-$R_5$ is independently selected from hydrogen, halogen, and $C_1$-$C_5$ alkyl; and wherein the compound of Formula II is prepared according to a method comprising
  i) forming a mixture comprising
    a) a compound of Formula I, wherein

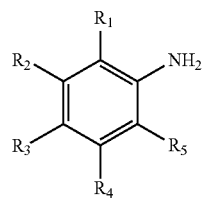
(Formula I)

each of $R_1$-$R_5$ is independently selected from hydrogen, halogen, and $C_1$-$C_5$ alkyl;
  b) chloral hydrate;
  c) a hydroxylamine derivative;
  d) a solvent;
  e) an inorganic salt; and
  f) an acid; and
  ii) reacting the mixture; and
  B) an acid; and
  II) reacting the mixture.

In one aspect, provided herein is a method of preparing a compound of Formula II, wherein

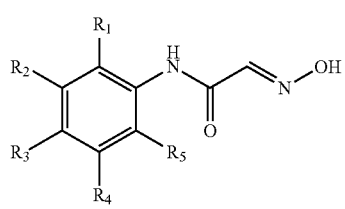
(Formula II)

each of $R_1$-$R_5$ is independently selected from hydrogen, halogen, and $C_1$-$C_5$ alkyl, the method comprising
  I) forming a mixture comprising
    A) a compound of Formula I, wherein

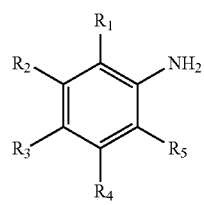
(Formula I)

each of $R_1$-$R_5$ is independently selected from hydrogen, halogen, and $C_1$-$C_5$ alkyl;
  B) chloral hydrate;
  C) a hydroxylamine derivative;
  D) a solvent;
  E) an inorganic salt; and
  F) an acid; and
  II) reacting the mixture.

In one aspect, provided herein is a method of preparing a compound of Formula IV, wherein

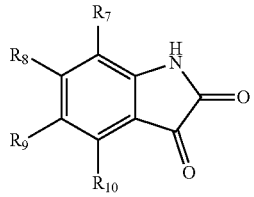

(Formula IV)

each of $R_7$-$R_{10}$ is independently selected from hydrogen, halogen, halogenated $C_1$-$C_5$ alkyl, and $C_1$-$C_5$ alkyl;
wherein at least one of $R_7$-$R_{10}$ is a halogen, the method comprising
I) forming a mixture comprising
   A) a compound of Formula II, wherein

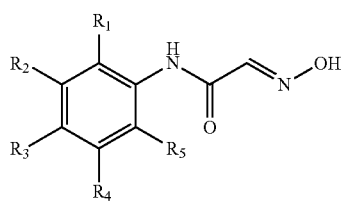

(Formula II)

each of $R_1$-$R_5$ is independently selected from hydrogen, halogen, and $C_1$-$C_5$ alkyl; and
   B) an acid;
II) reacting the first mixture;
III) introducing a halogenation reagent to the first mixture to form a second mixture; and
IV) reacting the second mixture.

DETAILED DESCRIPTION OF THE DISCLOSURE

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where an invention or a portion thereof is defined with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used herein, the term "about" means plus or minus 10% of the value.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different.

When a group contains a substituent which can be hydrogen, for example $R^4$, then, when this substituent is taken as hydrogen, it is recognized that this is equivalent to said group being unsubstituted.

The term "alkyl" includes, without limitation, a functional group comprising straight-chain or branched alkyl. In some aspects, the alkyl may be methyl, ethyl, n-propyl, i-propyl, or the different butyl, pentyl or hexyl isomers.

Certain compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers.

The embodiments of this disclosure include:

Embodiment 1. A method of preparing a compound of Formula VI, wherein

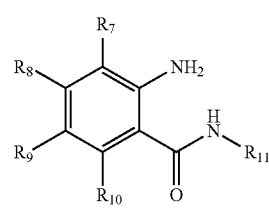

(Formula VI)

each of $R_7$-$R_{10}$ is independently selected from hydrogen, halogen, halogenated $C_1$-$C_5$ alkyl, and $C_1$-$C_5$ alkyl;
wherein at least one of $R_7$-$R_{10}$ is a halogen; and
wherein $R_{11}$ is selected from branched $C_1$-$C_{10}$ alkyl and unbranched $C_1$-$C_{10}$ alkyl, the method comprising I) forming a mixture comprising
   A) a compound of Formula V, wherein

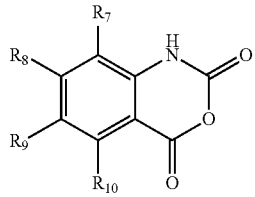
(Formula V)

each of $R_7$-$R_{10}$ is independently selected from hydrogen, halogen, halogenated $C_1$-$C_5$ alkyl, and $C_1$-$C_5$ alkyl;
wherein at least one of $R_7$-$R_{10}$ is a halogen; and
wherein the compound of Formula V is prepared according to a method comprising
   i) forming a first mixture comprising
      a) a compound of Formula III, wherein

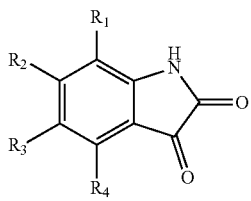
(Formula III)

each of $R_1$-$R_4$ is independently selected from hydrogen, halogen, and $C_1$-$C_5$ alkyl;
      b) a solvent; and
      c) a halogenation reagent;
   ii) reacting the first mixture;
   iii) introducing a second mixture to the first mixture to form a third mixture, the second mixture comprising
      d) an oxidation agent; and
      e) a catalyst; and
   iv) reacting the third mixture;
   B) an alkylamine; and
   C) a solvent; and
II) reacting the mixture.

Embodiment 2. The method of embodiment 1, wherein the alkylamine comprises a functional group selected from branched $C_1$-$C_{10}$ alkyl and unbranched $C_1$-$C_{10}$ alkyl.

Embodiment 3. The method of embodiment 2, wherein the alkylamine is selected from methylamine, ethylamine, propylamine, isopropylamine, butylamine, t-butylamine, and combinations thereof.

Embodiment 4. The method of embodiment 3, wherein the alkylamine is methylamine.

Embodiment 5. The method of embodiment 1, wherein the solvent C) is selected from acetonitrile, dichloroethane, toluene, chlorobenzene, xylene, methanol, ethanol, isopropanol, ethyl acetate, isopropyl acetate, and combinations thereof.

Embodiment 6. The method of embodiment 5, wherein the solvent C) is ethyl acetate.

Embodiment 7. The method of embodiment 1, wherein the method step II) of reacting the mixture occurs at a reaction temperature in the range of about 0° C. to about 100° C.

Embodiment 8. The method of embodiment 7, wherein the method step II) of reacting the mixture occurs at a reaction temperature in the range of about 20° C. to about 30° C.

Embodiment 9. The method of embodiment 1, wherein the solvent b) is selected from acetonitrile, dichloroethane, toluene, chlorobenzene, xylene, acetic acid, acetic anhydride, propionic acid, butyric acid, and combinations thereof.

Embodiment 10. The method of embodiment 9, wherein the solvent b) is acetic acid.

Embodiment 11. The method of embodiment 1, wherein the halogenation reagent is selected from a chlorination reagent, a bromination reagent, an iodination reagent, and combinations thereof.

Embodiment 12. The method of embodiment 11, wherein the chlorination reagent is selected from chlorine, thionyl chloride, phosgene, diphosgene, triphosgene, oxalyl chloride, sulfuryl chloride, phosphorus trichloride, phosphorus oxychloride, trichloroisocyanuric acid, and combinations thereof.

Embodiment 13. The method of embodiment 12, wherein the chlorination reagent is sulfuryl chloride.

Embodiment 14. The method of embodiment 1, wherein the method step ii) of reacting the first mixture occurs at a reaction temperature in the range of about 20° C. to about 140° C.

Embodiment 15. The method of embodiment 14, wherein the method step ii) of reacting the first mixture occurs at a reaction temperature in the range of about 120° C. to about 130° C.

Embodiment 16. The method of embodiment 1, wherein the oxidation agent is selected from oxygen, chlorine, sodium hypochlorite, chromium trioxide, 3-chloroperoxybenzoic acid, hydrogen peroxide, peroxyacetic acid, potassium peroxymonosulfate, potassium permanganate, and combinations thereof.

Embodiment 17. The method of embodiment 16, wherein the oxidation agent is hydrogen peroxide.

Embodiment 18. The method of embodiment 1, wherein the catalyst is selected from sulfuric acid, hydrogen chloride, nitric acid, and combinations thereof.

Embodiment 19. The method of embodiment 18, wherein the catalyst is sulfuric acid.

Embodiment 20. The method of embodiment 1, wherein the method step iv) of reacting the third mixture occurs at a reaction temperature in the range of about 20° C. to about 100° C.

Embodiment 21. The method of embodiment 20, wherein the method step iv) of reacting the third mixture occurs at a reaction temperature in the range of about 60° C. to about 65° C.

Embodiment 22. The method of embodiment 1, wherein the compound of Formula III is prepared according to a method comprising
   I) forming a mixture comprising
      A) a compound of Formula II, wherein

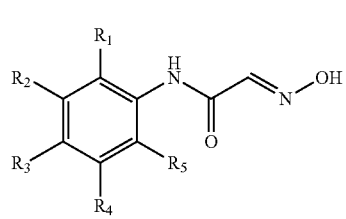
(Formula II)

each of $R_1$-$R_5$ is independently selected from hydrogen, halogen, and $C_1$-$C_5$ alkyl; and
wherein the compound of Formula II is prepared according to a method comprising
i) forming a mixture comprising
  a) a compound of Formula I, wherein

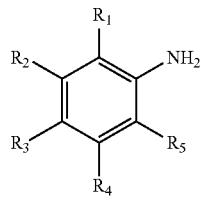
(Formula I)

each of $R_1$-$R_5$ is independently selected from hydrogen, halogen, and $C_1$-$C_5$ alkyl;
  b) chloral hydrate;
  c) a hydroxylamine derivative;
  d) a solvent;
  e) an inorganic salt; and
  f) an acid; and
ii) reacting the mixture; and
B) an acid; and
II) reacting the mixture.

Embodiment 23. The method of embodiment 22, wherein the acid B) is selected from hydrochloric acid, sulfuric acid, nitric acid, acetic acid, and combinations thereof.

Embodiment 24. The method of embodiment 23, wherein the acid B) is hydrochloric acid.

Embodiment 25. The method of embodiment 22, wherein the method step II) of reacting the mixture occurs at a reaction temperature in the range of about 10° C. to about 90° C.

Embodiment 26. The method of embodiment 25, wherein the method step II) of reacting the mixture occurs at a reaction temperature in the range of about 60° C. to about 65° C.

Embodiment 27. The method of embodiment 22, wherein the hydroxylamine derivative is selected from hydroxylamine sulfate, hydroxylamine hydrochloride, and combinations thereof.

Embodiment 28. The method of embodiment 27, wherein the hydroxylamine derivative is hydroxylamine sulfate.

Embodiment 29. The method of embodiment 22, wherein the solvent is selected from methanol, ethanol, toluene, water, and combinations thereof.

Embodiment 30. The method of embodiment 29, wherein the solvent is water.

Embodiment 31. The method of embodiment 22, wherein the inorganic salt is selected from sodium sulfate, sodium hydrogen sulfate, sodium chloride, sodium disulfite, potassium sulfate, potassium chloride, and combinations thereof.

Embodiment 32. The method of embodiment 31, wherein the inorganic salt is sodium sulfate.

Embodiment 33. The method of embodiment 22, wherein the acid f) is selected from hydrochloric acid, sulfuric acid, nitric acid, hydrobromic acid, formic acid, acetic acid, and combinations thereof.

Embodiment 34. The method of embodiment 33, wherein the acid f) is hydrochloric acid.

Embodiment 35. The method of embodiment 22, wherein the concentration of the compound of Formula I in the mixture ranges from about 1% to about 30%.

Embodiment 36. The method of embodiment 35, wherein the concentration of the compound of Formula I in the mixture is in the range of about 3% to about 10%.

Embodiment 37. The method of embodiment 22, wherein the method step ii) of reacting the mixture occurs at a reaction temperature in the range of about 10° C. to about 100° C.

Embodiment 38. The method of embodiment 37, wherein the method step ii) of reacting the mixture occurs at a reaction temperature in the range of about 50° C. to about 55° C.

Embodiment 39. A method of preparing a compound of Formula V, wherein

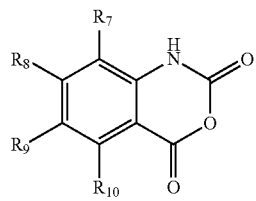
(Formula V)

each of $R_7$-$R_{10}$ is independently selected from hydrogen, halogen, halogenated $C_1$-$C_5$ alkyl, and $C_1$-$C_5$ alkyl; and
wherein at least one of $R_7$-$R_{10}$ is a halogen, the method comprising
I) forming a first mixture comprising
  A) a compound of Formula III, wherein

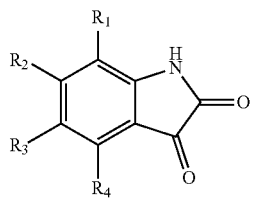
(Formula III)

each of $R_1$-$R_4$ is independently selected from hydrogen, halogen, and $C_1$-$C_5$ alkyl;
  B) a solvent; and
  C) a halogenation reagent;
II) reacting the first mixture;
III) introducing a second mixture to the first mixture to form a third mixture, the second mixture comprising
  D) an oxidation agent; and
  E) a catalyst; and
IV) reacting the third mixture.

Embodiment 40. The method of embodiment 39, wherein the solvent is selected from acetonitrile, dichloroethane, toluene, chlorobenzene, xylene, acetic acid, acetic anhydride, propionic acid, butyric acid, and combinations thereof.

Embodiment 41. The method of embodiment 40, wherein the solvent is acetic acid.

Embodiment 42. The method of embodiment 39, wherein the halogenation reagent is selected from a chlorination reagent, a bromination reagent, an iodination reagent, and combinations thereof.

Embodiment 43. The method of embodiment 42, wherein the chlorination reagent is selected from chlorine, thionyl chloride, phosgene, diphosgene, triphosgene, oxalyl chloride, sulfuryl chloride, phosphorus trichloride, phosphorus oxychloride, trichloroisocyanuric acid, and combinations thereof.

Embodiment 44. The method of embodiment 43, wherein the chlorination reagent is sulfuryl chloride.

Embodiment 45. The method of embodiment 39, wherein the method step II) of reacting the first mixture occurs at a reaction temperature in the range of about 20° C. to about 140° C.

Embodiment 46. The method of embodiment 45, wherein the method step II) of reacting the first mixture occurs at a reaction temperature in the range of about 120° C. to about 130° C.

Embodiment 47. The method of embodiment 39, wherein the oxidation agent is selected from oxygen, chlorine, sodium hypochlorite, chromium trioxide, 3-chloroperoxybenzoic acid, hydrogen peroxide, peroxyacetic acid, potassium peroxymonosulfate, potassium permanganate, and combinations thereof.

Embodiment 48. The method of embodiment 47, wherein the oxidation agent is hydrogen peroxide.

Embodiment 49. The method of embodiment 39, wherein the catalyst is selected from sulfuric acid, hydrogen chloride, nitric acid, and combinations thereof.

Embodiment 50. The method of embodiment 49, wherein the catalyst is sulfuric acid.

Embodiment 51. The method of embodiment 39, wherein the method step IV) of reacting the third mixture occurs at a reaction temperature in the range of about 20° C. to about 100° C.

Embodiment 52. The method of embodiment 51, wherein the method step IV) of reacting the third mixture occurs at a reaction temperature in the range of about 60° C. to about 65° C.

Embodiment 53. The method of embodiment 39, wherein the compound of Formula III is prepared according to a method comprising
I) forming a mixture comprising
A) a compound of Formula II, wherein

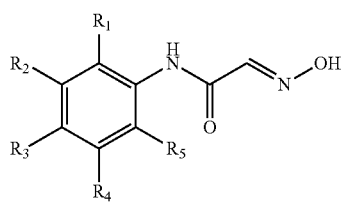

(Formula II)

each of $R_1$-$R_5$ is independently selected from hydrogen, halogen, and $C_1$-$C_5$ alkyl; and
wherein the compound of Formula II is prepared according to a method comprising
i) forming a mixture comprising
a) a compound of Formula I, wherein

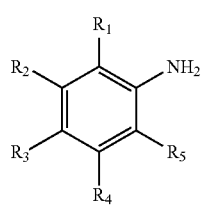

(Formula I)

each of $R_1$-$R_5$ is independently selected from hydrogen, halogen, and $C_1$-$C_5$ alkyl;
b) chloral hydrate;
c) a hydroxylamine derivative;
d) a solvent;
e) an inorganic salt; and
f) an acid; and
ii) reacting the mixture; and
B) an acid; and
II) reacting the mixture.

Embodiment 54. The method of embodiment 53, wherein the acid B) is selected from hydrochloric acid, sulfuric acid, nitric acid, acetic acid, and combinations thereof.

Embodiment 55. The method of embodiment 54, wherein the acid B) is hydrochloric acid.

Embodiment 56. The method of embodiment 53, wherein the method step II) of reacting the mixture occurs at a reaction temperature in the range of about 10° C. to about 90° C.

Embodiment 57. The method of embodiment 56, wherein the method step II) of reacting the mixture occurs at a reaction temperature in the range of about 60° C. to about 65° C.

Embodiment 58. The method of embodiment 53, wherein the hydroxylamine derivative is selected from hydroxylamine sulfate, hydroxylamine hydrochloride, and combinations thereof.

Embodiment 59. The method of embodiment 58, wherein the hydroxylamine derivative is hydroxylamine sulfate.

Embodiment 60. The method of embodiment 53, wherein the solvent is selected from methanol, ethanol, toluene, water, and combinations thereof.

Embodiment 61. The method of embodiment 60, wherein the solvent is water.

Embodiment 62. The method of embodiment 53, wherein the inorganic salt is selected from sodium sulfate, sodium hydrogen sulfate, sodium chloride, sodium disulfite, potassium sulfate, potassium chloride, and combinations thereof.

Embodiment 63. The method of embodiment 62, wherein the inorganic salt is sodium sulfate.

Embodiment 64. The method of embodiment 53, wherein the acid f) is selected from hydrochloric acid, sulfuric acid, nitric acid, hydrobromic acid, formic acid, acetic acid, and combinations thereof.

Embodiment 65. The method of embodiment 64, wherein the acid f) is hydrochloric acid.

Embodiment 66. The method of embodiment 53, wherein the concentration of the compound of Formula I in the mixture ranges from about 1% to about 30%.

Embodiment 67. The method of embodiment 66, wherein the concentration of the compound of Formula I in the mixture is in the range of about 3% to about 10%.

Embodiment 68. The method of embodiment 53, wherein the method step ii) of reacting the mixture occurs at a reaction temperature in the range of about 10° C. to about 100° C.

Embodiment 69. The method of embodiment 68, wherein the method step ii) of reacting the mixture occurs at a reaction temperature in the range of about 50° C. to about 55° C.

Embodiment 70. A method of preparing a compound of Formula VI, wherein

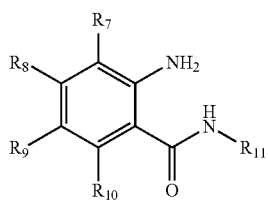
(Formula VI)

each of $R_7$-$R_{10}$ is independently selected from hydrogen, halogen, halogenated $C_1$-$C_5$ alkyl, and $C_1$-$C_5$ alkyl;
wherein at least one of $R_7$-$R_{10}$ is a halogen; and
wherein $R_{11}$ is selected from branched $C_1$-$C_{10}$ alkyl and unbranched $C_1$-$C_{10}$ alkyl, the method comprising
  I) forming a mixture comprising
    A) a compound of Formula V, wherein

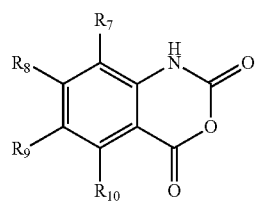
(Formula V)

each of $R_7$-$R_{10}$ is independently selected from hydrogen, halogen, halogenated $C_1$-$C_5$ alkyl, and $C_1$-$C_5$ alkyl;
wherein at least one of $R_7$-$R_{10}$ is a halogen; and
wherein the compound of Formula V is prepared according to a method comprising
  i) forming a mixture comprising
    a) a compound of Formula IV, wherein

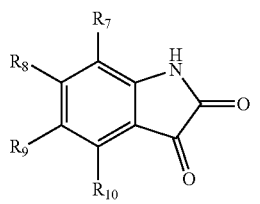
(Formula IV)

each of $R_7$-$R_{10}$ is independently selected from hydrogen, halogen, halogenated $C_1$-$C_5$ alkyl, and $C_1$-$C_5$ alkyl; and
wherein at least one of $R_7$-$R_{10}$ is a halogen;
    b) an oxidation agent;
    c) a solvent; and
    d) a catalyst; and
  ii) reacting the mixture;
  B) an alkylamine; and
  C) a solvent; and
II) reacting the mixture.

Embodiment 71. The method of embodiment 70, wherein the alkylamine comprises a functional group selected from branched $C_1$-$C_{10}$ alkyl and unbranched $C_1$-$C_{10}$ alkyl.

Embodiment 72. The method of embodiment 71, wherein the alkylamine is selected from methylamine, ethylamine, propylamine, isopropylamine, butylamine, t-butylamine, and combinations thereof.

Embodiment 73. The method of embodiment 72, wherein the alkylamine is methylamine.

Embodiment 74. The method of embodiment 70, wherein the solvent C) is selected from acetonitrile, dichloroethane, toluene, chlorobenzene, xylene, methanol, ethanol, isopropanol, ethyl acetate, isopropyl acetate, and combinations thereof.

Embodiment 75. The method of embodiment 74, wherein the solvent C) is ethyl acetate.

Embodiment 76. The method of embodiment 70, wherein the method step II) of reacting the mixture occurs at a reaction temperature in the range of about 0° C. to about 100° C.

Embodiment 77. The method of embodiment 76, wherein the method step II) of reacting the mixture occurs at a reaction temperature in the range of about 20° C. to about 30° C.

Embodiment 78. The method of embodiment 70, wherein the oxidation agent is selected from oxygen, chlorine, sodium hypochlorite, chromium trioxide, 3-chloroperoxybenzoic acid, hydrogen peroxide, peroxyacetic acid, potassium peroxymonosulfate, potassium permanganate, and combinations thereof.

Embodiment 79. The method of embodiment 78, wherein the oxidation agent is hydrogen peroxide.

Embodiment 80. The method of embodiment 70, wherein the solvent c) is selected from acetonitrile, methanol, ethanol, isopropanol, water, dimethylformamide, dimethyl sulfoxide, N-Methylpyrrolidone, tetrahydrofuran, acetic acid, acetic anhydride, propionic acid, butyric acid, and combinations thereof.

Embodiment 81. The method of embodiment 80, wherein the solvent c) is acetic acid.

Embodiment 82. The method of embodiment 70, wherein the catalyst is selected from sulfuric acid, hydrogen chloride, nitric acid, and combinations thereof.

Embodiment 83. The method of embodiment 82, wherein the catalyst is sulfuric acid.

Embodiment 84. The method of embodiment 70, wherein the method step ii) of reacting the mixture occurs at a reaction temperature in the range of about 20° C. to about 100° C.

Embodiment 85. The method of embodiment 84, wherein the method step ii) of reacting the mixture occurs at a reaction temperature in the range of about 60° C. to about 65° C.

Embodiment 86. The method of embodiment 70, wherein the compound of Formula IV is prepared according to a method comprising
  I) forming a mixture comprising
    A) a compound of Formula III, wherein

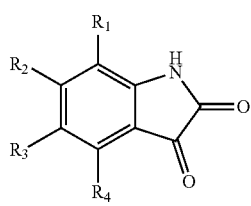
(Formula III)

each of $R_1$-$R_4$ is independently selected from hydrogen, halogen, and $C_1$-$C_5$ alkyl;

B) a solvent;
C) a halogenation reagent; and
II) reacting the mixture.

Embodiment 87. The method of embodiment 86, wherein the solvent is selected from acetonitrile, dichloroethane, toluene, chlorobenzene, xylene, acetic acid, acetic anhydride, propionic acid, butyric acid, and combinations thereof.

Embodiment 88. The method of embodiment 87, wherein the solvent is acetic acid.

Embodiment 89. The method of embodiment 86, wherein the halogenation reagent is selected from a chlorination reagent, a bromination reagent, an iodination reagent, and combinations thereof.

Embodiment 90. The method of embodiment 89, wherein the chlorination reagent is selected from chlorine, thionyl chloride, phosgene, diphosgene, triphosgene, oxalyl chloride, sulfuryl chloride, phosphorus trichloride, phosphorus oxychloride, trichloroisocyanuric acid, and combinations thereof.

Embodiment 91. The method of embodiment 90, wherein the chlorination reagent is sulfuryl chloride.

Embodiment 92. The method of embodiment 86, wherein the method step II) of reacting the mixture occurs at a reaction temperature in the range of about 20° C. to about 140° C.

Embodiment 93. The method of embodiment 92, wherein the method step II) of reacting the mixture occurs at a reaction temperature in the range of about 120° C. to about 130° C.

Embodiment 94. The method of embodiment 86, wherein the compound of Formula III is prepared according to a method comprising
I) forming a mixture comprising
A) a compound of Formula II, wherein

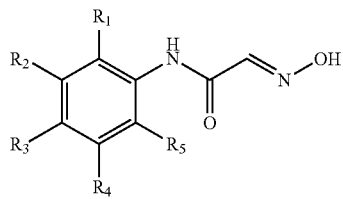

(Formula II)

each of $R_1$-$R_5$ is independently selected from hydrogen, halogen, and $C_1$-$C_5$ alkyl; and
wherein the compound of Formula II is prepared according to a method comprising
i) forming a mixture comprising
a) a compound of Formula I, wherein

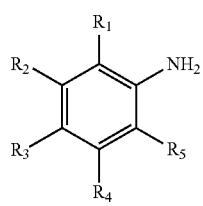

(Formula I)

each of $R_1$-$R_5$ is independently selected from hydrogen, halogen, and $C_1$-$C_5$ alkyl;

b) chloral hydrate;
c) a hydroxylamine derivative;
d) a solvent;
e) an inorganic salt; and
f) an acid; and
ii) reacting the mixture; and
B) an acid; and
II) reacting the mixture.

Embodiment 95. The method of embodiment 94, wherein the acid B) is selected from hydrochloric acid, sulfuric acid, nitric acid, acetic acid, and combinations thereof.

Embodiment 96. The method of embodiment 95, wherein the acid B) is hydrochloric acid.

Embodiment 97. The method of embodiment 94, wherein the method step II) of reacting the mixture occurs at a reaction temperature in the range of about 10° C. to about 90° C.

Embodiment 98. The method of embodiment 97, wherein the method step II) of reacting the mixture occurs at a reaction temperature in the range of about 60° C. to about 65° C.

Embodiment 99. The method of embodiment 94, wherein the hydroxylamine derivative is selected from hydroxylamine sulfate, hydroxylamine hydrochloride, and combinations thereof.

Embodiment 100. The method of embodiment 99, wherein the hydroxylamine derivative is hydroxylamine sulfate.

Embodiment 101. The method of embodiment 94, wherein the solvent is selected from methanol, ethanol, toluene, water, and combinations thereof.

Embodiment 102. The method of embodiment 101, wherein the solvent is water.

Embodiment 103. The method of embodiment 94, wherein the inorganic salt is selected from sodium sulfate, sodium hydrogen sulfate, sodium chloride, sodium disulfite, potassium sulfate, potassium chloride, and combinations thereof.

Embodiment 104. The method of embodiment 103, wherein the inorganic salt is sodium sulfate.

Embodiment 105. The method of embodiment 94, wherein the acid f) is selected from hydrochloric acid, sulfuric acid, nitric acid, hydrobromic acid, formic acid, acetic acid, and combinations thereof.

Embodiment 106. The method of embodiment 105, wherein the acid f) is hydrochloric acid.

Embodiment 107. The method of embodiment 94, wherein the concentration of the compound of Formula I in the mixture ranges from about 1% to about 30%.

Embodiment 108. The method of embodiment 107, wherein the concentration of the compound of Formula I in the mixture is in the range of about 3% to about 10%.

Embodiment 109. The method of embodiment 94, wherein the method step ii) of reacting the mixture occurs at a reaction temperature in the range of about 10° C. to about 100° C.

Embodiment 110. The method of embodiment 109, wherein the method step ii) of reacting the mixture occurs at a reaction temperature in the range of about 50° C. to about 55° C.

Embodiment 111. The method of embodiment 70, wherein the compound of Formula IV is prepared according to a method comprising I) forming a mixture comprising
A) a compound of Formula II, wherein

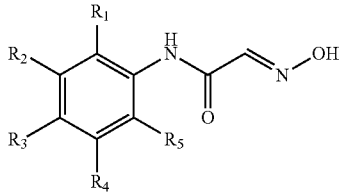

(Formula II)

each of $R_1$-$R_5$ is independently selected from hydrogen, halogen, and $C_1$-$C_5$ alkyl; and
B) an acid;
II) reacting the first mixture;
III) introducing a halogenation reagent to the first mixture to form a second mixture; and
IV) reacting the second mixture.

Embodiment 112. The method of embodiment 111, wherein the acid is selected from sulfuric acid, acetic acid, and combinations thereof.

Embodiment 113. The method of embodiment 112, wherein the acid is sulfuric acid.

Embodiment 114. The method of embodiment 111, wherein the halogenation reagent is selected from a chlorination reagent, a bromination reagent, an iodination reagent, and combinations thereof.

Embodiment 115. The method of embodiment 114, wherein the chlorination reagent is selected from chlorine, thionyl chloride, phosgene, diphosgene, triphosgene, oxalyl chloride, sulfuryl chloride, phosphorus trichloride, phosphorus oxychloride, trichloroisocyanuric acid, and combinations thereof.

Embodiment 116. The method of embodiment 115, wherein the chlorination reagent is trichloroisocyanuric acid.

Embodiment 117. The method of embodiment 111, wherein the method step IV) of reacting the second mixture occurs at a reaction temperature in the range of about 10° C. to about 100° C.

Embodiment 118. The method of embodiment 117, wherein the method step IV) of reacting the second mixture occurs at a reaction temperature in the range of about 10° C. to about 65° C.

Embodiment 119. The method of embodiment 111, wherein the compound of Formula II is prepared according to a method comprising
i) forming a mixture comprising
a) a compound of Formula I, wherein

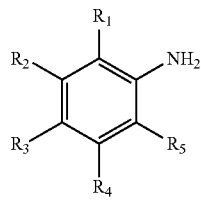

(Formula I)

each of $R_1$-$R_5$ is independently selected from hydrogen, halogen, and $C_1$-$C_5$ alkyl;

b) chloral hydrate;
c) a hydroxylamine derivative;
d) a solvent;
e) an inorganic salt; and
f) an acid; and
ii) reacting the mixture.

Embodiment 120. The method of embodiment 119, wherein the hydroxylamine derivative is selected from hydroxylamine sulfate, hydroxylamine hydrochloride, and combinations thereof.

Embodiment 121. The method of embodiment 120, wherein the hydroxylamine derivative is hydroxylamine sulfate.

Embodiment 122. The method of embodiment 119, wherein the solvent is selected from methanol, ethanol, toluene, water, and combinations thereof.

Embodiment 123. The method of embodiment 122, wherein the solvent is water.

Embodiment 124. The method of embodiment 119, wherein the inorganic salt is selected from sodium sulfate, sodium hydrogen sulfate, sodium chloride, sodium disulfite, potassium sulfate, potassium chloride, and combinations thereof.

Embodiment 125. The method of embodiment 124, wherein the inorganic salt is sodium sulfate.

Embodiment 126. The method of embodiment 119, wherein the acid is selected from hydrochloric acid, sulfuric acid, nitric acid, hydrobromic acid, formic acid, acetic acid, and combinations thereof.

Embodiment 127. The method of embodiment 126, wherein the acid is hydrochloric acid.

Embodiment 128. The method of embodiment 119, wherein the concentration of the compound of Formula I in the mixture ranges from about 1% to about 30%.

Embodiment 129. The method of embodiment 128, wherein the concentration of the compound of Formula I in the mixture is in the range of about 3% to about 10%.

Embodiment 130. The method of embodiment 119, wherein the method step of reacting the mixture occurs at a reaction temperature in the range of about 10° C. to about 100° C.

Embodiment 131. The method of embodiment 130, wherein the method step of reacting the mixture occurs at a reaction temperature in the range of about 50° C. to about 55° C.

Embodiment 132. A method of preparing a compound of Formula V, wherein

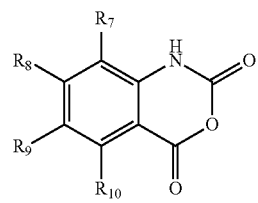

(Formula V)

each of $R_7$-$R_{10}$ is independently selected from hydrogen, halogen, halogenated $C_1$-$C_5$ alkyl, and $C_1$-$C_5$ alkyl; and
wherein at least one of $R_7$-$R_{10}$ is a halogen, the method comprising I) forming a mixture comprising
A) a compound of Formula IV, wherein (Formula IV)

each of $R_7$-$R_{10}$ is independently selected from hydrogen, halogen, halogenated $C_1$-$C_5$ alkyl, and $C_1$-$C_5$ alkyl; and
wherein at least one of $R_7$-$R_{10}$ is a halogen;
B) an oxidation agent;
C) a solvent; and
D) a catalyst; and
II) reacting the mixture.

Embodiment 133. The method of embodiment 132, wherein the oxidation agent is selected from oxygen, chlorine, sodium hypochlorite, chromium trioxide, 3-chloroperoxybenzoic acid, hydrogen peroxide, peroxyacetic acid, potassium peroxymonosulfate, potassium permanganate, and combinations thereof.

Embodiment 134. The method of embodiment 133, wherein the oxidation agent is hydrogen peroxide.

Embodiment 135. The method of embodiment 132, wherein the solvent is selected from acetonitrile, methanol, ethanol, isopropanol, water, dimethylformamide, dimethyl sulfoxide, N-Methylpyrrolidone, tetrahydrofuran, acetic acid, acetic anhydride, propionic acid, butyric acid, and combinations thereof.

Embodiment 136. The method of embodiment 135, wherein the solvent is acetic acid.

Embodiment 137. The method of embodiment 132, wherein the catalyst is selected from sulfuric acid, hydrogen chloride, nitric acid, and combinations thereof.

Embodiment 138. The method of embodiment 137, wherein the catalyst is sulfuric acid.

Embodiment 139. The method of embodiment 132, wherein the method step II) of reacting the mixture occurs at a reaction temperature in the range of about 20° C. to about 100° C.

Embodiment 140. The method of embodiment 139, wherein the method step II) of reacting the mixture occurs at a reaction temperature in the range of about 60° C. to about 65° C.

Embodiment 141. The method of embodiment 132, wherein the compound of Formula IV is prepared according to a method comprising
I) forming a mixture comprising
A) a compound of Formula III, wherein (Formula III)

each of $R_1$-$R_4$ is independently selected from hydrogen, halogen, and $C_1$-$C_5$ alkyl;
B) a solvent;
C) a halogenation reagent; and
II) reacting the mixture.

Embodiment 142. The method of embodiment 141, wherein the solvent is selected from acetonitrile, dichloroethane, toluene, chlorobenzene, xylene, acetic acid, acetic anhydride, propionic acid, butyric acid, and combinations thereof.

Embodiment 143. The method of embodiment 142, wherein the solvent is acetic acid.

Embodiment 144. The method of embodiment 141, wherein the halogenation reagent is selected from a chlorination reagent, a bromination reagent, an iodination reagent, and combinations thereof.

Embodiment 145. The method of embodiment 144, wherein the chlorination reagent is selected from chlorine, thionyl chloride, phosgene, diphosgene, triphosgene, oxalyl chloride, sulfuryl chloride, phosphorus trichloride, phosphorus oxychloride, trichloroisocyanuric acid, and combinations thereof.

Embodiment 146. The method of embodiment 145, wherein the chlorination reagent is sulfuryl chloride.

Embodiment 147. The method of embodiment 141, wherein the method step II) of reacting the mixture occurs at a reaction temperature in the range of about 20° C. to about 140° C.

Embodiment 148. The method of embodiment 147, wherein the method step II) of reacting the mixture occurs at a reaction temperature in the range of about 120° C. to about 130° C.

Embodiment 149. The method of embodiment 141, wherein the compound of Formula III is prepared according to a method comprising
I) forming a mixture comprising
A) a compound of Formula II, wherein (Formula II)

each of $R_1$-$R_5$ is independently selected from hydrogen, halogen, and $C_1$-$C_5$ alkyl; and
wherein the compound of Formula II is prepared according to a method comprising
i) forming a mixture comprising
a) a compound of Formula I, wherein (Formula I)

23 each of $R_1$-$R_5$ is independently selected from hydrogen, halogen, and $C_1$-$C_5$ alkyl;
b) chloral hydrate;
c) a hydroxylamine derivative;
d) a solvent;
e) an inorganic salt; and
f) an acid; and
ii) reacting the mixture; and
B) an acid; and
II) reacting the mixture.

Embodiment 150. The method of embodiment 149, wherein the acid B) is selected from hydrochloric acid, sulfuric acid, nitric acid, acetic acid, and combinations thereof.

Embodiment 151. The method of embodiment 150, wherein the acid B) is hydrochloric acid.

Embodiment 152. The method of embodiment 149, wherein the method step II) of reacting the mixture occurs at a reaction temperature in the range of about 10° C. to about 90° C.

Embodiment 153. The method of embodiment 152, wherein the method step II) of reacting the mixture occurs at a reaction temperature in the range of about 60° C. to about 65° C.

Embodiment 154. The method of embodiment 149, wherein the hydroxylamine derivative is selected from hydroxylamine sulfate, hydroxylamine hydrochloride, and combinations thereof.

Embodiment 155. The method of embodiment 154, wherein the hydroxylamine derivative is hydroxylamine sulfate.

Embodiment 156. The method of embodiment 149, wherein the solvent is selected from methanol, ethanol, toluene, water, and combinations thereof.

Embodiment 157. The method of embodiment 156, wherein the solvent is water.

Embodiment 158. The method of embodiment 149, wherein the inorganic salt is selected from sodium sulfate, sodium hydrogen sulfate, sodium chloride, sodium disulfite, potassium sulfate, potassium chloride, and combinations thereof.

Embodiment 159. The method of embodiment 158, wherein the inorganic salt is sodium sulfate.

Embodiment 160. The method of embodiment 149, wherein the acid f) is selected from hydrochloric acid, sulfuric acid, nitric acid, hydrobromic acid, formic acid, acetic acid, and combinations thereof.

Embodiment 161. The method of embodiment 160, wherein the acid f) is hydrochloric acid.

Embodiment 162. The method of embodiment 149, wherein the concentration of the compound of Formula I in the mixture ranges from about 1% to about 30%.

Embodiment 163. The method of embodiment 162, wherein the concentration of the compound of Formula I in the mixture is in the range of about 3% to about 10%.

Embodiment 164. The method of embodiment 149, wherein the method step ii) of reacting the mixture occurs at a reaction temperature in the range of about 10° C. to about 100° C.

Embodiment 165. The method of embodiment 164, wherein the method step ii) of reacting the mixture occurs at a reaction temperature in the range of about 50° C. to about 55° C.

Embodiment 166. The method of embodiment 132, wherein the compound of Formula IV is prepared according to a method comprising

24

I) forming a mixture comprising
A) a compound of Formula II, wherein

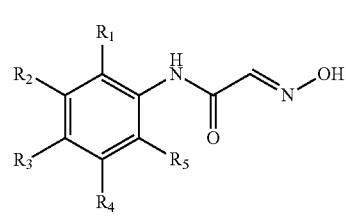
(Formula II)

each of $R_1$-$R_5$ is independently selected from hydrogen, halogen, and $C_1$-$C_5$ alkyl; and
B) an acid;
II) reacting the first mixture;
III) introducing a halogenation reagent to the first mixture to form a second mixture; and
IV) reacting the second mixture.

Embodiment 167. The method of embodiment 166, wherein the acid is selected from sulfuric acid, acetic acid, and combinations thereof.

Embodiment 168. The method of embodiment 167, wherein the acid is sulfuric acid.

Embodiment 169. The method of embodiment 166, wherein the halogenation reagent is selected from a chlorination reagent, a bromination reagent, an iodination reagent, and combinations thereof.

Embodiment 170. The method of embodiment 169, wherein the chlorination reagent is selected from chlorine, thionyl chloride, phosgene, diphosgene, triphosgene, oxalyl chloride, sulfuryl chloride, phosphorus trichloride, phosphorus oxychloride, trichloroisocyanuric acid, and combinations thereof.

Embodiment 171. The method of embodiment 170, wherein the chlorination reagent is trichloroisocyanuric acid.

Embodiment 172. The method of embodiment 166, wherein the method step IV) of reacting the second mixture occurs at a reaction temperature in the range of about 10° C. to about 100° C.

Embodiment 173. The method of embodiment 172, wherein the method step IV) of reacting the second mixture occurs at a reaction temperature in the range of about 10° C. to about 65° C.

Embodiment 174. The method of embodiment 166, wherein the compound of Formula II is prepared according to a method comprising
i) forming a mixture comprising
a) a compound of Formula I, wherein

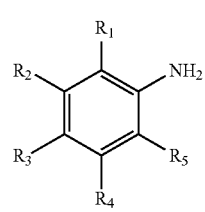
(Formula I)

each of $R_1$-$R_5$ is independently selected from hydrogen, halogen, and $C_1$-$C_5$ alkyl;
b) chloral hydrate;
c) a hydroxylamine derivative;

d) a solvent;

e) an inorganic salt; and f) an acid; and ii) reacting the mixture.

Embodiment 175. The method of embodiment 174, wherein the hydroxylamine derivative is selected from hydroxylamine sulfate, hydroxylamine hydrochloride, and combinations thereof.

Embodiment 176. The method of embodiment 175, wherein the hydroxylamine derivative is hydroxylamine sulfate.

Embodiment 177. The method of embodiment 174, wherein the solvent is selected from methanol, ethanol, toluene, water, and combinations thereof.

Embodiment 178. The method of embodiment 177, wherein the solvent is water.

Embodiment 179. The method of embodiment 174, wherein the inorganic salt is selected from sodium sulfate, sodium hydrogen sulfate, sodium chloride, sodium disulfite, potassium sulfate, potassium chloride, and combinations thereof.

Embodiment 180. The method of embodiment 179, wherein the inorganic salt is sodium sulfate.

Embodiment 181. The method of embodiment 174, wherein the acid is selected from hydrochloric acid, sulfuric acid, nitric acid, hydrobromic acid, formic acid, acetic acid, and combinations thereof.

Embodiment 182. The method of embodiment 181, wherein the acid is hydrochloric acid.

Embodiment 183. The method of embodiment 174, wherein the concentration of the compound of Formula I in the mixture ranges from about 1% to about 30%.

Embodiment 184. The method of embodiment 183, wherein the concentration of the compound of Formula I in the mixture is in the range of about 3% to about 10%.

Embodiment 185. The method of embodiment 174, wherein the method step of reacting the mixture occurs at a reaction temperature in the range of about 10° C. to about 100° C.

Embodiment 186. The method of embodiment 185, wherein the method step of reacting the mixture occurs at a reaction temperature in the range of about 50° C. to about 55° C.

Embodiment 187. A method of preparing a compound of Formula IV, wherein (Formula IV)

each of $R_7$-$R_{10}$ is independently selected from hydrogen, halogen, halogenated $C_1$-$C_5$ alkyl, and $C_1$-$C_5$ alkyl;

wherein at least one of $R_7$-$R_{10}$ is a halogen, the method comprising

I) forming a mixture comprising

A) a compound of Formula III, wherein (Formula III)

each of $R_1$-$R_4$ is independently selected from hydrogen, halogen, and $C_1$-$C_5$ alkyl;

B) a solvent;

C) a halogenation reagent; and

II) reacting the mixture.

Embodiment 188. The method of embodiment 187, wherein the solvent is selected from acetonitrile, dichloroethane, toluene, chlorobenzene, xylene, acetic acid, acetic anhydride, propionic acid, butyric acid, and combinations thereof.

Embodiment 189. The method of embodiment 188, wherein the solvent is acetic acid.

Embodiment 190. The method of embodiment 187, wherein the halogenation reagent is selected from a chlorination reagent, a bromination reagent, an iodination reagent, and combinations thereof.

Embodiment 191. The method of embodiment 190, wherein the chlorination reagent is selected from chlorine, thionyl chloride, phosgene, diphosgene, triphosgene, oxalyl chloride, sulfuryl chloride, phosphorus trichloride, phosphorus oxychloride, trichloroisocyanuric acid, and combinations thereof.

Embodiment 192. The method of embodiment 191, wherein the chlorination reagent is sulfuryl chloride.

Embodiment 193. The method of embodiment 187, wherein the method step II) of reacting the mixture occurs at a reaction temperature in the range of about 20° C. to about 140° C.

Embodiment 194. The method of embodiment 193, wherein the method step II) of reacting the mixture occurs at a reaction temperature in the range of about 120° C. to about 130° C.

Embodiment 195. The method of embodiment 187, wherein the compound of Formula III is prepared according to a method comprising I) forming a mixture comprising A) a compound of Formula II, wherein (Formula II)

each of $R_1$-$R_5$ is independently selected from hydrogen, halogen, and $C_1$-$C_5$ alkyl; and wherein the compound of Formula II is prepared according to a method comprising i) forming a mixture comprising
   a) a compound of Formula I, wherein

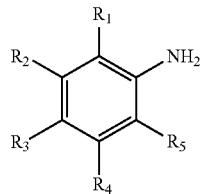

(Formula I)

each of $R_1$-$R_5$ is independently selected from hydrogen, halogen, and $C_1$-$C_5$ alkyl;
   b) chloral hydrate;
   c) a hydroxylamine derivative;
   d) a solvent;
   e) an inorganic salt; and
   f) an acid; and
ii) reacting the mixture; and
B) an acid; and
II) reacting the mixture.

Embodiment 196. The method of embodiment 195, wherein the acid B) is selected from hydrochloric acid, sulfuric acid, nitric acid, acetic acid, and combinations thereof.

Embodiment 197. The method of embodiment 196, wherein the acid B) is hydrochloric acid.

Embodiment 198. The method of embodiment 195, wherein the method step II) of reacting the mixture occurs at a reaction temperature in the range of about 10° C. to about 90° C.

Embodiment 199. The method of embodiment 198, wherein the method step II) of reacting the mixture occurs at a reaction temperature in the range of about 60° C. to about 65° C.

Embodiment 200. The method of embodiment 195, wherein the hydroxylamine derivative is selected from hydroxylamine sulfate, hydroxylamine hydrochloride, and combinations thereof.

Embodiment 201. The method of embodiment 200, wherein the hydroxylamine derivative is hydroxylamine sulfate.

Embodiment 202. The method of embodiment 195, wherein the solvent is selected from methanol, ethanol, toluene, water, and combinations thereof.

Embodiment 203. The method of embodiment 202, wherein the solvent is water.

Embodiment 204. The method of embodiment 195, wherein the inorganic salt is selected from sodium sulfate, sodium hydrogen sulfate, sodium chloride, sodium disulfite, potassium sulfate, potassium chloride, and combinations thereof.

Embodiment 205. The method of embodiment 204, wherein the inorganic salt is sodium sulfate.

Embodiment 206. The method of embodiment 195, wherein the acid f) is selected from hydrochloric acid, sulfuric acid, nitric acid, hydrobromic acid, formic acid, acetic acid, and combinations thereof.

Embodiment 207. The method of embodiment 206, wherein the acid f) is hydrochloric acid.

Embodiment 208. The method of embodiment 195, wherein the concentration of the compound of Formula I in the mixture ranges from about 1% to about 30%.

Embodiment 209. The method of embodiment 208, wherein the concentration of the compound of Formula I in the mixture is in the range of about 3% to about 10%.

Embodiment 210. The method of embodiment 195, wherein the method step ii) of reacting the mixture occurs at a reaction temperature in the range of about 10° C. to about 100° C.

Embodiment 211. The method of embodiment 210, wherein the method step ii) of reacting the mixture occurs at a reaction temperature in the range of about 50° C. to about 55° C.

Embodiment 212. A method of preparing a compound of Formula III, wherein

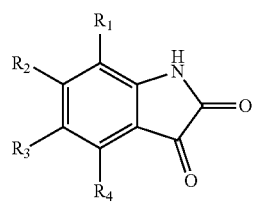

(Formula III)

each of $R_1$-$R_4$ is independently selected from hydrogen, halogen, and $C_1$-$C_5$ alkyl, the method comprising
I) forming a mixture comprising
   A) a compound of Formula II, wherein

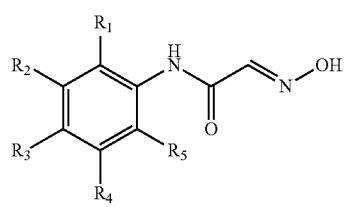

(Formula II)

each of $R_1$-$R_5$ is independently selected from hydrogen, halogen, and $C_1$-$C_5$ alkyl; and
wherein the compound of Formula II is prepared according to a method comprising
   i) forming a mixture comprising
      a) a compound of Formula I, wherein

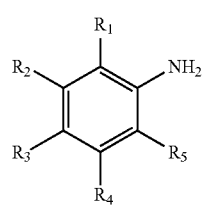

(Formula I)

each of $R_1$-$R_5$ is independently selected from hydrogen, halogen, and $C_1$-$C_5$ alkyl;
   b) chloral hydrate;
   c) a hydroxylamine derivative;
   d) a solvent;

e) an inorganic salt; and f) an acid; and ii) reacting the mixture; and

B) an acid; and

II) reacting the mixture.

Embodiment 213. The method of embodiment 212, wherein the acid B) is selected from hydrochloric acid, sulfuric acid, nitric acid, acetic acid, and combinations thereof.

Embodiment 214. The method of embodiment 213, wherein the acid B) is hydrochloric acid.

Embodiment 215. The method of embodiment 212, wherein the method step II) of reacting the mixture occurs at a reaction temperature in the range of about 10° C. to about 90° C.

Embodiment 216. The method of embodiment 215, wherein the method step II) of reacting the mixture occurs at a reaction temperature in the range of about 60° C. to about 65° C.

Embodiment 217. The method of embodiment 212, wherein the hydroxylamine derivative is selected from hydroxylamine sulfate, hydroxylamine hydrochloride, and combinations thereof.

Embodiment 218. The method of embodiment 217, wherein the hydroxylamine derivative is hydroxylamine sulfate.

Embodiment 219. The method of embodiment 212, wherein the solvent is selected from methanol, ethanol, toluene, water, and combinations thereof.

Embodiment 220. The method of embodiment 219, wherein the solvent is water.

Embodiment 221. The method of embodiment 212, wherein the inorganic salt is selected from sodium sulfate, sodium hydrogen sulfate, sodium chloride, sodium disulfite, potassium sulfate, potassium chloride, and combinations thereof.

Embodiment 222. The method of embodiment 221, wherein the inorganic salt is sodium sulfate.

Embodiment 223. The method of embodiment 212, wherein the acid f) is selected from hydrochloric acid, sulfuric acid, nitric acid, hydrobromic acid, formic acid, acetic acid, and combinations thereof.

Embodiment 224. The method of embodiment 223, wherein the acid f) is hydrochloric acid.

Embodiment 225. The method of embodiment 212, wherein the concentration of the compound of Formula I in the mixture ranges from about 1% to about 30%.

Embodiment 226. The method of embodiment 225, wherein the concentration of the compound of Formula I in the mixture is in the range of about 3% to about 10%.

Embodiment 227. The method of embodiment 212, wherein the method step ii) of reacting the mixture occurs at a reaction temperature in the range of about 10° C. to about 100° C.

Embodiment 228. The method of embodiment 227, wherein the method step ii) of reacting the mixture occurs at a reaction temperature in the range of about 50° C. to about 55° C.

Embodiment 229. A method of preparing a compound of Formula II, wherein

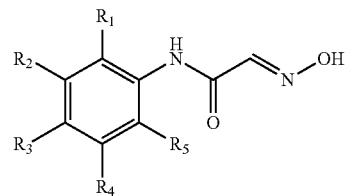

(Formula II)

each of $R_1$-$R_5$ is independently selected from hydrogen, halogen, and $C_1$-$C_5$ alkyl, the method comprising I) forming a mixture comprising A) a compound of Formula I, wherein

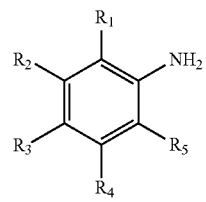

(Formula I)

each of $R_1$-$R_5$ is independently selected from hydrogen, halogen, and $C_1$-$C_5$ alkyl;

B) chloral hydrate;

C) a hydroxylamine derivative;

D) a solvent;

E) an inorganic salt; and

F) an acid; and

II) reacting the mixture.

Embodiment 230. The method of embodiment 229, wherein the hydroxylamine derivative is selected from hydroxylamine sulfate, hydroxylamine hydrochloride, and combinations thereof.

Embodiment 231. The method of embodiment 230, wherein the hydroxylamine derivative is hydroxylamine sulfate.

Embodiment 232. The method of embodiment 229, wherein the solvent is selected from methanol, ethanol, toluene, water, and combinations thereof.

Embodiment 233. The method of embodiment 232, wherein the solvent is water.

Embodiment 234. The method of embodiment 229, wherein the inorganic salt is selected from sodium sulfate, sodium hydrogen sulfate, sodium chloride, sodium disulfite, potassium sulfate, potassium chloride, and combinations thereof.

Embodiment 235. The method of embodiment 234, wherein the inorganic salt is sodium sulfate.

Embodiment 236. The method of embodiment 229, wherein the acid is selected from hydrochloric acid, sulfuric acid, nitric acid, hydrobromic acid, formic acid, acetic acid, and combinations thereof.

Embodiment 237. The method of embodiment 236, wherein the acid is hydrochloric acid.

Embodiment 238. The method of embodiment 229, wherein the concentration of the compound of Formula I in the mixture ranges from about 1% to about 30%.

Embodiment 239. The method of embodiment 238, wherein the concentration of the compound of Formula I in the mixture is in the range of about 3% to about 10%.

Embodiment 240. The method of embodiment 229, wherein the method step of reacting the mixture occurs at a reaction temperature in the range of about 10° C. to about 100° C.

Embodiment 241. The method of embodiment 240, wherein the method step of reacting the mixture occurs at a reaction temperature in the range of about 50° C. to about 55° C.

Embodiment 242. A method of preparing a compound of Formula IV, wherein (Formula IV)

each of $R_7$-$R_{10}$ is independently selected from hydrogen, halogen, halogenated $C_1$-$C_5$ alkyl, and $C_1$-$C_5$ alkyl;
wherein at least one of $R_7$-$R_{10}$ is a halogen, the method comprising
I) forming a first mixture comprising
   A) a compound of Formula II, wherein (Formula II)

each of $R_1$-$R_5$ is independently selected from hydrogen, halogen, and $C_1$-$C_5$ alkyl; and
   B) an acid;
II) reacting the first mixture;
III) introducing a halogenation reagent to the first mixture to form a second mixture; and
IV) reacting the second mixture.

Embodiment 243. The method of embodiment 242, wherein the acid is selected from sulfuric acid, acetic acid, and combinations thereof.

Embodiment 244. The method of embodiment 243, wherein the acid is sulfuric acid.

Embodiment 245. The method of embodiment 242, wherein the halogenation reagent is selected from a chlorination reagent, a bromination reagent, an iodination reagent, and combinations thereof.

Embodiment 246. The method of embodiment 245, wherein the chlorination reagent is selected from chlorine, thionyl chloride, phosgene, diphosgene, triphosgene, oxalyl chloride, sulfuryl chloride, phosphorus trichloride, phosphorus oxychloride, trichloroisocyanuric acid, and combinations thereof.

Embodiment 247. The method of embodiment 246, wherein the chlorination reagent is trichloroisocyanuric acid.

Embodiment 248. The method of embodiment 242, wherein the method step IV) of reacting the second mixture occurs at a reaction temperature in the range of about 10° C. to about 100° C.

Embodiment 249. The method of embodiment 248, wherein the method step IV) of reacting the second mixture occurs at a reaction temperature in the range of about 10° C. to about 65° C.

Embodiment 250. The method of embodiment 242, wherein the compound of Formula II is prepared according to a method comprising
i) forming a mixture comprising
   a) a compound of Formula I, wherein (Formula I)

each of $R_1$-$R_5$ is independently selected from hydrogen, halogen, and $C_1$-$C_5$ alkyl;
   b) chloral hydrate;
   c) a hydroxylamine derivative;
   d) a solvent;
   e) an inorganic salt; and
   f) an acid; and
ii) reacting the mixture.

Embodiment 251. The method of embodiment 250, wherein the hydroxylamine derivative is selected from hydroxylamine sulfate, hydroxylamine hydrochloride, and combinations thereof.

Embodiment 252. The method of embodiment 251, wherein the hydroxylamine derivative is hydroxylamine sulfate.

Embodiment 253. The method of embodiment 250, wherein the solvent is selected from methanol, ethanol, toluene, water, and combinations thereof.

Embodiment 254. The method of embodiment 253, wherein the solvent is water.

Embodiment 255. The method of embodiment 250, wherein the inorganic salt is selected from sodium sulfate, sodium hydrogen sulfate, sodium chloride, sodium disulfite, potassium sulfate, potassium chloride, and combinations thereof.

Embodiment 256. The method of embodiment 255, wherein the inorganic salt is sodium sulfate.

Embodiment 257. The method of embodiment 250, wherein the acid is selected from hydrochloric acid, sulfuric acid, nitric acid, hydrobromic acid, formic acid, acetic acid, and combinations thereof.

Embodiment 258. The method of embodiment 257, wherein the acid is hydrochloric acid.

Embodiment 259. The method of embodiment 250, wherein the concentration of the compound of Formula I in the mixture ranges from about 1% to about 30%.

Embodiment 260. The method of embodiment 259, wherein the concentration of the compound of Formula I in the mixture is in the range of about 3% to about 10%.

Embodiment 261. The method of embodiment 250, wherein the method step of reacting the mixture occurs at a reaction temperature in the range of about 10° C. to about 100° C.

Embodiment 262. The method of embodiment 261, wherein the method step of reacting the mixture occurs at a reaction temperature in the range of about 50° C. to about 55° C.

In one aspect, a compound of Formula VI is prepared according to a method represented by Scheme 1. The R groups are as defined anywhere in this disclosure.

Scheme 1.

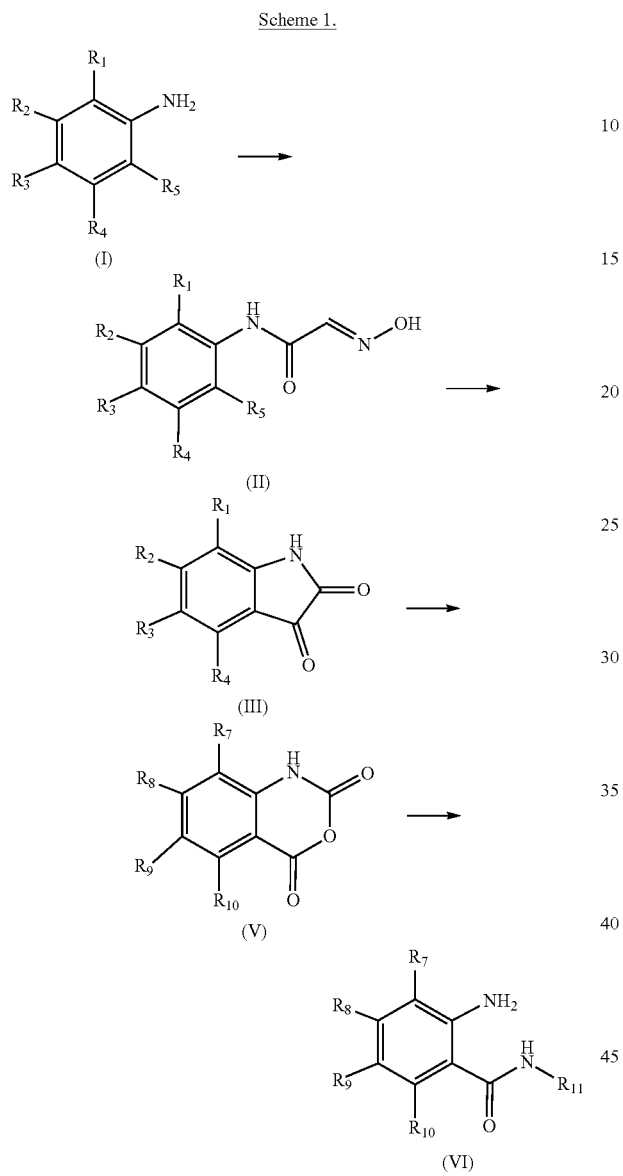

In one aspect, a compound of Formula VI is prepared according to a method represented by Scheme 2. The R groups are as defined anywhere in this disclosure.

Scheme 2.

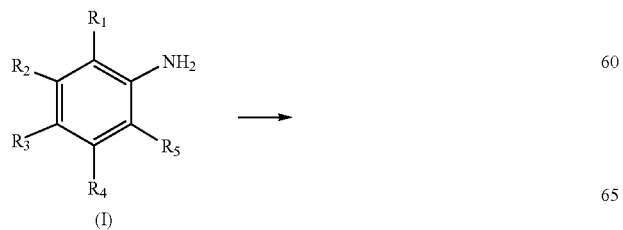

-continued

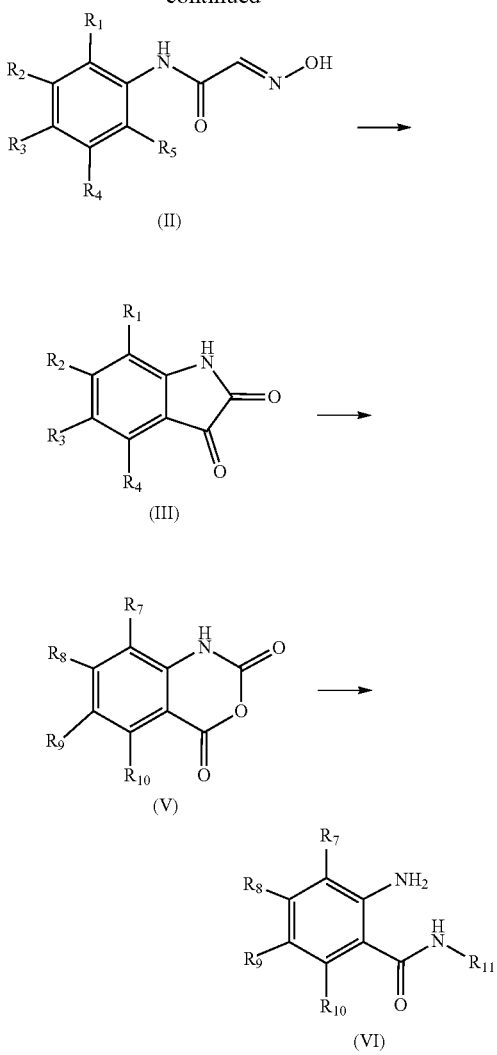

In one aspect, a compound of Formula VI is prepared according to a method represented by Scheme 3. The R groups are as defined anywhere in this disclosure.

Scheme 3.

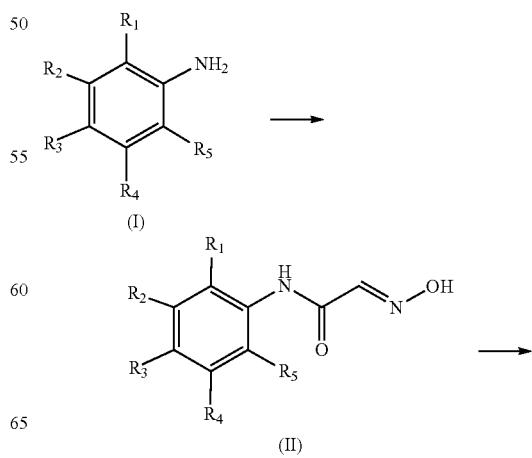

-continued
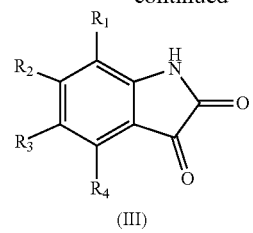
(III)
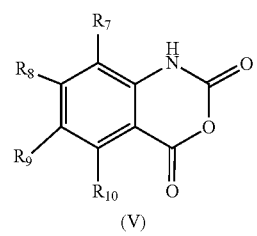
(V)
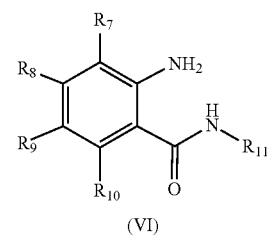
(VI)
In one aspect, 2-amino-5-chloro-N,3-dimethylbenzamide is prepared according to a method represented by Scheme 4.
Scheme 4.
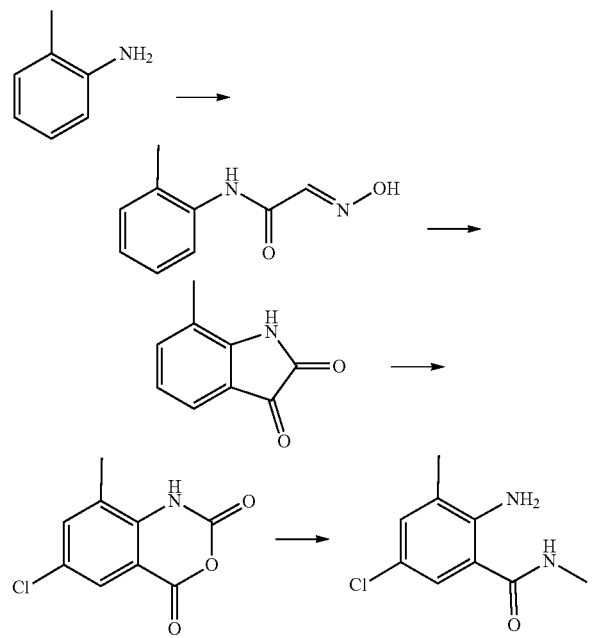
In one aspect, 2-amino-5-chloro-N,3-dimethylbenzamide is prepared according to a method represented by Scheme 5.
Scheme 5.
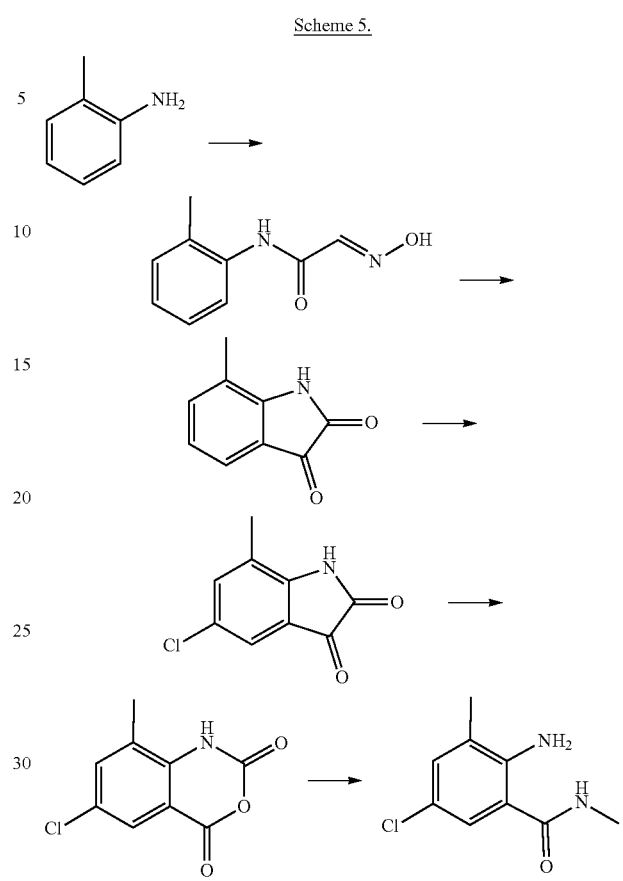
In one aspect, 2-amino-5-chloro-N,3-dimethylbenzamide is prepared according to a method represented by Scheme 6.
Scheme 6.
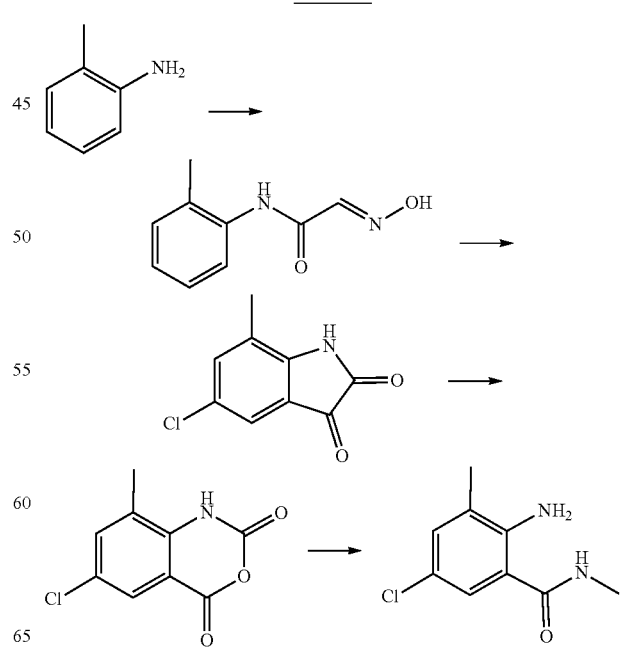

In one aspect, a compound of Formula II is prepared according to a method represented by Scheme 7. The R groups are as defined anywhere in this disclosure.

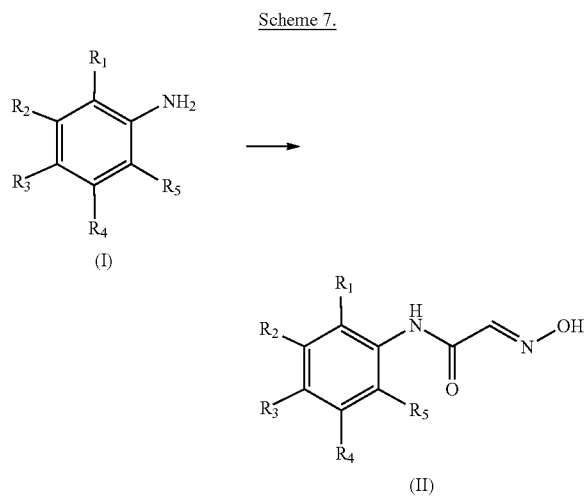

Scheme 7.

This aspect includes reacting a compound of Formula I with chloral hydrate and hydroxylamine sulfate in a solvent at a reaction concentration in the presence of an inorganic salt and an acid. In one embodiment, the compound of Formula I is toluidine. In one embodiment, the solvent is selected from MeOH, EtOH, toluene, water, and combinations thereof. In another embodiment, the solvent is water. In one embodiment, the inorganic salt is selected from sodium sulfate, sodium hydrogen sulfate, sodium chloride, sodium disulfite, potassium sulfate, potassium chloride, and combinations thereof. In another embodiment, the inorganic salt is sodium sulfate. In one embodiment, the acid is selected from hydrogen chloride, sulfuric acid, nitric acid, hydrobromic acid, formic acid, acetic acid, and combinations thereof. In another embodiment, the acid is hydrogen chloride. In one embodiment, the reaction concentration is in the range from about 1% to about 30% for the compound of Formula I. In another embodiment, the reaction concentration is in the range from about 3% to about 10% for the compound of Formula I. In one embodiment, the reaction temperature is in the range from about 10° C. to about 100° C. In another embodiment, the reaction temperature is in the range from about 50° C. to about 55° C.

When reaction conditions of a reaction temperature of 90° C. in water are applied to a compound of Formula I, wherein the compound of Formula I is toluidine, (E)-2-(hydroxyimino)-N-(o-tolyl)acetamide is obtained as a sticky solid, leading to a difficult and poor separation. Furthermore, swift increases in temperature are caused when adding this crude (E)-2-(hydroxyimino)-N-(o-tolyl)acetamide by portions in subsequent reaction steps. This problem is overcome in the present disclosure by decreasing the reaction temperature in water from 90° C. to a temperature in the range from about 50 to about 55° C. This change not only results in pure (E)-2-(hydroxyimino)-N-(o-tolyl)acetamide with good morphotype, but also advantageously increases the reaction concentration. This high reaction concentration decreases waste water and cost.

In one aspect, a compound of Formula III is prepared according to a method represented by Scheme 8. The R groups are as defined anywhere in this disclosure.

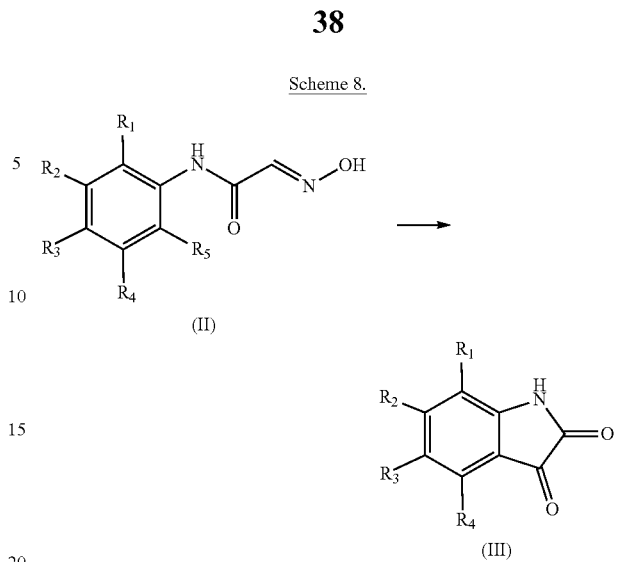

Scheme 8.

This aspect includes reacting a compound of Formula II with an acid that is also used as a solvent. In one embodiment, the acid is selected from hydrochloric acid, sulfuric acid, nitric acid, acetic acid, and combinations thereof. In another embodiment, the acid is sulfuric acid. In one embodiment, the reaction temperature is in the range from about 10° C. to about 90° C. In another embodiment, the reaction temperature is in the range from about 60° C. to 65° C.

In one aspect, a compound of Formula IV is prepared according to a method represented by Scheme 9. The R groups are as defined anywhere in this disclosure.

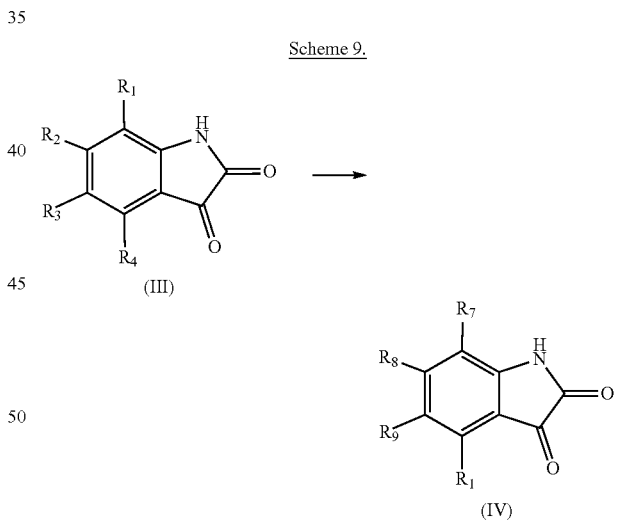

Scheme 9.

This aspect includes reacting a compound of Formula III with a halogenation reagent in a solvent. In one embodiment, the halogenation reagent is selected from fluorination agents, chlorination agents, bromination agents, iodination agents, and combinations thereof. In one embodiment, the halogenation reagent is a chlorination reagent selected from chlorine, thionyl chloride, phosgene, diphosgene, triphosgene, oxalyl chloride, sulfuryl chloride, phosphorus trichloride, phosphorus oxychloride, trichloroisocyanuric acid, and combinations thereof. In another embodiment, the chlorination reagent is sulfuryl chloride. In one embodiment, the solvent is selected from acetonitrile (ACN), 1,2-dichloroethane (DCE), toluene, chlorobenzene, xylene, acetic acid, acetic anhydride, propionic acid, butyric acid, and combinations thereof. In another embodiment, the solvent is acetic acid. In one embodiment, the reaction temperature is in the range from about 20° C. to about 140° C. In another embodiment, the reaction temperature is in the range from about 120° C. to about 130° C.

In one aspect, a compound of Formula IV is prepared according to a method represented by Scheme 10. The R groups are as defined anywhere in this disclosure.

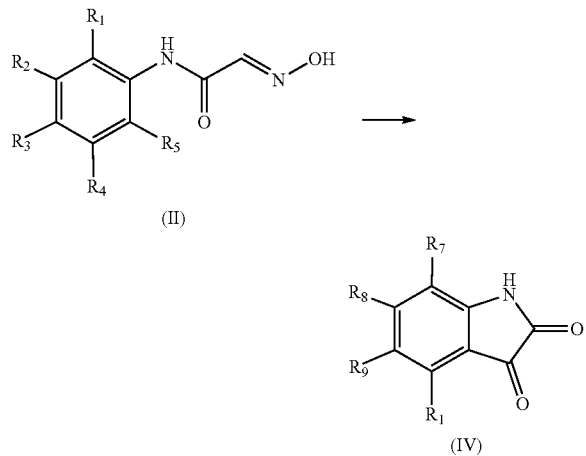

This aspect includes reacting, in a first reaction, a compound of Formula II with an acid that is also used as a solvent, followed by adding a halogenation agent and, in a second reaction, forming a compound of Formula IV. In one embodiment, the acid is selected from acetic acid, sulfuric acid, and combinations thereof. In another embodiment, the acid is sulfuric acid. In one embodiment, the halogenation reagent is selected from fluorination agents, chlorination agents, bromination agents, iodination agents, and combinations thereof. In one embodiment, the halogenation reagent is a chlorination reagent selected from chlorine, thionyl chloride, phosgene, diphosgene, triphosgene, oxalyl chloride, sulfuryl chloride, phosphorus trichloride, phosphorus oxychloride, trichloroisocyanuric acid, and combinations thereof. In another embodiment, the chlorination reagent is trichloroisocyanuric acid. In one embodiment, the reaction temperature of the first reaction is in the range of about 0° C. to about 100° C. In another embodiment, the reaction temperature of the first reaction is in the range of about 10° C. to about 65° C. In one embodiment, the reaction temperature of the second reaction is in the range from about 10° C. to about 100° C.

In another embodiment, the reaction temperature of the second reaction is in the range from about 10° C. to 65° C.

This aspect is a single-pot process and possesses several advantages. First, the need to separate intermediates produced from the compound of Formula II, such as the compound of Formula III, before subsequent reactions is eliminated. Second, potential losses of intermediates produced from the compound of Formula II, such as the compound of Formula III, are reduced. Third, the total yield is increased. Fourth, the number of reaction steps and workup operations is reduced. Fifth, overall cost is reduced.

In one aspect, a compound of Formula V is prepared according to a method represented by Scheme 11. The R groups are as defined anywhere in this disclosure.

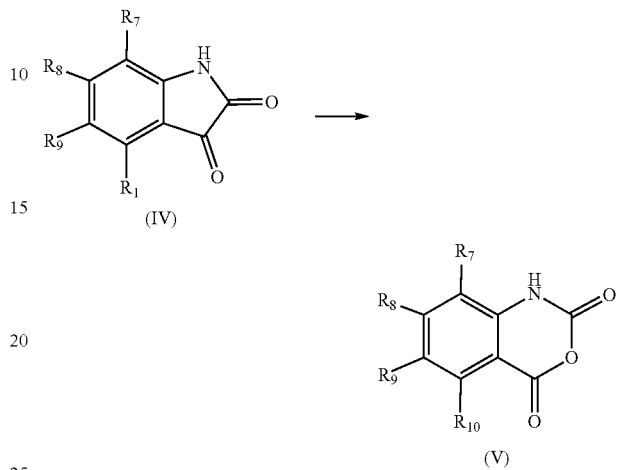

This aspect includes adding an oxidation agent to an aqueous solution that includes a compound of Formula IV in the presence of catalysis. In one embodiment, the oxidation agent is selected from oxygen, chlorine, sodium hypochlorite, chromium trioxide, 3-chloroperoxybenzoic acid, hydrogen peroxide, peroxyacetic acid, potassium peroxymonosulfate, potassium permanganate, and combinations thereof. In another embodiment, the oxidation agent is hydrogen peroxide. In one embodiment, the solvent is selected from acetonitrile (ACN), methanol (MeOH), ethanol (EtOH), isopropyl alcohol (i-PrOH), water ($H_2O$), dimethylformamide (DMF), dimethyl sulfoxide (DMSO), N-methyl-2-pyrrolidone (NMP), tetrahydrofuran (THF), acetic acid, acetic anhydride, propionic acid, butyric acid, and combinations thereof. In another embodiment, the solvent is acetic acid. In one embodiment, the catalyst is selected from sulfuric acid, hydrogen chloride, nitric acid, and combinations thereof. In another embodiment, the catalyst is sulfuric acid. In one embodiment, the reaction temperature is in the range from about 20° C. to about 100° C. In another embodiment, the reaction temperature is in the range from about 60° C. to about 65° C.

In one aspect, a compound of Formula VI is prepared according to a method represented by Scheme 12. The R groups are as defined anywhere in this disclosure.

Scheme 12.

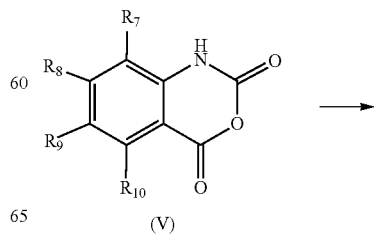

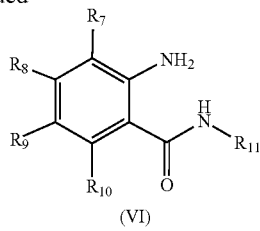

(VI)

This aspect includes reacting a compound of Formula V with an alkylamine in a solvent. In one embodiment, the alkylamine comprises a functional group selected from branched $C_1$-$C_{10}$ alkyl and unbranched $C_1$-$C_{10}$ alkyl. In another embodiment, the alkylamine is selected from methylamine, ethylamine, propylamine, isopropylamine, butylamine, t-butylamine, and combinations thereof. In one embodiment, the solvent is selected from acetonitrile (ACN), 1,2-dichloroethane (DCE), toluene, chlorobenzene, xylene, methanol (MeOH), ethanol (EtOH), isopropyl alcohol (i-PrOH), ethyl acetate (EtOAc), isopropyl acetate (IPAc), and combinations thereof. In another embodiment, the solvent is EtOAc. In one embodiment, the reaction temperature is in the range from about 0° C. to about 100° C. In another embodiment, the reaction temperature is in the range from about 20° C. to about 30° C.

In one aspect, a compound of Formula V is prepared according to a method represented by Scheme 13. The R groups are as defined anywhere in this disclosure.

Scheme 13.

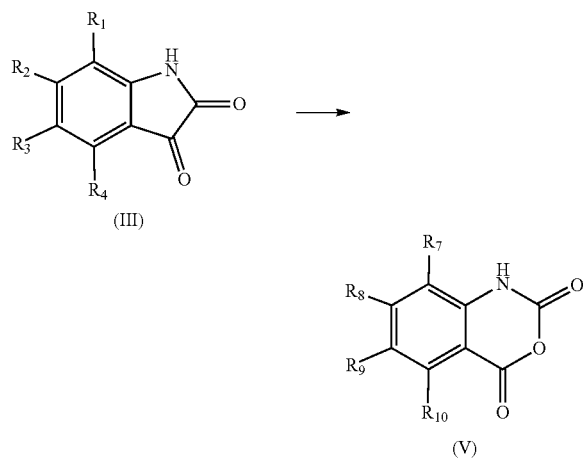

This aspect includes reacting a compound of Formula III with a halogenation reagent in a solvent, followed by adding an oxidation agent to the solution in the presence of a catalyst. In one embodiment, the halogenation reagent is selected from fluorination agents, chlorination agents, bromination agents, iodination agents, and combinations thereof. In another embodiment, the halogenation reagent is a chlorination agent selected from chlorine, thionyl chloride, phosgene, diphosgene, triphosgene, oxalyl chloride, sulfuryl chloride, phosphorus trichloride, phosphorus oxychloride, trichloroisocyanuric acid, and combinations thereof. In another embodiment, the halogenation reagent is sulfuryl chloride. In one embodiment, the solvent is selected from ACN, DCE, toluene, chlorobenzene, xylene, acetic acid, acetic anhydride, propionic acid and butyric acid. In another embodiment, the solvent is acetic acid. In one embodiment, the reaction temperature for the halogenation is in the range from about 20° C. to about 140° C. In another embodiment, the reaction temperature for halogenation is in the range from about 120° C. to about 130° C. In one embodiment, the oxidation agent is selected from oxygen, chlorine, sodium hypochlorite, chromium trioxide, 3-chloroperoxybenzoic acid, hydrogen peroxide, peroxyacetic acid, potassium peroxymonosulfate, potassium permanganate, and combinations thereof. In another embodiment, the oxidation agent is hydrogen peroxide. In one embodiment, the catalyst is selected from sulfuric acid, hydrogen chloride, nitric acid, potassium hydroxide, and combinations thereof. In another embodiment, the catalyst is sulfuric acid. In one embodiment, the reaction temperature for oxidation is in the range from about 20° C. to about 100° C. In another embodiment, the reaction temperature for oxidation is in the range from about 60° C. to about 65° C.

This aspect is a single-pot process and possesses several advantages. First, the need to separate intermediates produced from the compound of Formula III, such as the compound of Formula IV, before subsequent reactions is eliminated. Second, potential losses of intermediates produced from the compound of Formula III, such as the compound of Formula IV, are reduced. Third, the total yield is increased. Fourth, the number of reaction steps and workup operations is reduced. Fifth, overall cost is reduced.

EXAMPLES

Without further elaboration, it is believed that one skilled in the art using the preceding description can utilize the present invention to its fullest extent. The following Examples are, therefore, to be construed as merely illustrative, and not limiting of the disclosure in any way whatsoever. The starting material for the following Examples may not have necessarily been prepared by a particular preparative run whose procedure is described in other Examples. It also is understood that any numerical range recited herein includes all values from the lower value to the upper value. For example, if a range is stated as 10-50, it is intended that values such as 12-30, 20-40, or 30-50, etc., are expressly enumerated in this specification. These are only examples of what is specifically intended, and all possible combinations of numerical values between and including the lowest value and the highest value enumerated are to be considered to be expressly stated in this application.

Example 1. Reaction of o-Toluidine 11.5 g of o-toluidine, 12.0 g of hydrochloric acid, 19.7 g of chloral hydrate, 27.0 g of hydroxylamine sulfate, 30.0 g of sodium sulfate, and 200.0 g of water were charged to a reactor. The reaction temperature was controlled at 55-60° C. After reaction, the mixture was cooled to room temperature and filtrated. The filter cake was washed with water and dried. 13.2 g of high purity of (E)-3-hydroxy-N-(o-tolyl)acrylamide was obtained.

Example 2. Cyclization 20.0 g of (E)-3-hydroxy-N-(o-tolyl)acrylamide was charged by portions, to control the reaction temperature, to sulfuric acid in a reactor. The reaction temperature was controlled between 60° C. and 65° C. After reaction, the mixture was cooled to room temperature and added to ice water. The mixture was stirred and filtrated. The filter cake was washed with water and dried. 16.0 g of 7-methylindoline-2,3-dione was obtained. This crude product could be used for subsequent reactions without additional processing.

Example 3. Halogenation 30.0 g of 7-methylindoline-2,3-dione, 50.3 g of sulfuryl chloride, and 100.0 g of acetic acid were charged to a reactor. The reaction temperature was controlled at 120-125° C. After reaction, the mixture was cooled to room temperature. Water was charged to the mixture, which was stirred at room temperature. The mixture was filtrated. The filter cake was washed by water and dried. 29.1 g of 5-chloro-7-methylindoline-2,3-dione was obtained.

Example 4. Oxidation 18.0 g of 5-chloro-7-methylindoline-2,3-dione, 100.0 g of acetic acid, and 1.0 g of sulfuric acid was charged to a reactor. The reaction temperature was controlled at 60-65° C. At this temperature, 13.0 g of 30% hydrogen peroxide solution was added dropwise to control the temperature between 60-65° C. After reaction, water was charged to the mixture, which was stirred at room temperature. The mixture was filtrated. The filter cake was washed by water and dried. 14.6 of 6-chloro-8-methyl-2H-benzo[d][1,3]oxazine-2,4(1H)-dione was obtained.

Example 5. Reaction with Methanamine 10.0 g of 6-chloro-8-methyl-2H-benzo[d][1,3]oxazine-2,4(1H)-dione and 100.0 g of ethyl acetate was charged to a reactor. Gaseous methanamine was bubbled to the reaction at room temperature. After reaction, the mixture was extracted by water. The organic phase solvent was removed under vacuum. 8.5 g of crude product of 2-amino-5-chloro-N,3-dimethylbenzamide was obtained.

Example 6. One-Pot Synthesis 30.0 g of 7-methylindoline-2,3-dione, 50.3 g of sulfuryl chloride, and 164.0 g of acetic acid was charged to a reactor. The reaction temperature was controlled at 120-125° C. After consumption of 7-methylindoline-2,3-dione, the reaction temperature was cooled to 60-65° C. 41.4 g of 30% hydrogen peroxide solution was added dropwise to control the temperature between 60-65° C. After reaction, water was charged to the mixture, which was stirred at room temperature. The mixture was filtrated. The filter cake was washed by water and dried. 27.6 g of 6-chloro-8-methyl-2H-benzo[d][1,3]oxazine-2,4(1H)-dione was obtained.

This written description uses examples to illustrate the present disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of preparing a compound of Formula VI, wherein

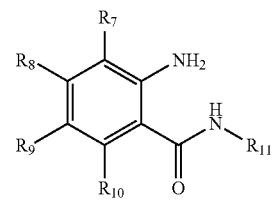

(Formula VI)

each of $R_7$-$R_{10}$ is independently selected from hydrogen, halogen, halogenated $C_1$-$C_5$ alkyl, and $C_1$-$C_5$ alkyl;
wherein at least one of $R_7$-$R_{10}$ is a halogen; and
wherein $R_{11}$ is selected from branched $C_1$-$C_{10}$ alkyl and unbranched $C_1$-$C_{10}$ alkyl, the method comprising
  I) forming a mixture comprising
    A) a compound of Formula V, wherein

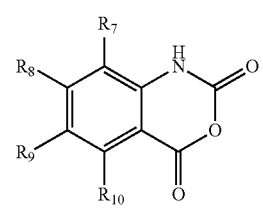

(Formula V)

each of $R_7$-$R_{10}$ is independently selected from hydrogen, halogen, halogenated $C_1$-$C_5$ alkyl, and $C_1$-$C_5$ alkyl;
wherein at least one of $R_7$-$R_{10}$ is a halogen; and
wherein the compound of Formula V is prepared according to a method comprising
  i) forming a first mixture comprising
    a) a compound of Formula III, wherein

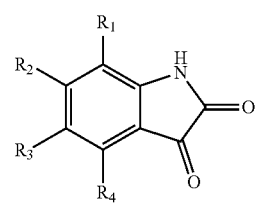

(Formula III)

each of $R_1$-$R_4$ is independently selected from hydrogen, halogen, and $C_1$-$C_5$ alkyl;
    b) a solvent; and
    c) a halogenation reagent;
  ii) reacting the first mixture;
  iii) adding an oxidation agent to the reacted first mixture in the presence of a catalyst to form a further mixture; and
  iv) reacting the third mixture;
    B) an alkylamine; and
    C) a solvent; and
  II) reacting the mixture.

2. The method of claim 1, wherein the method step II) of reacting the mixture occurs at a reaction temperature in the range of about 0° C. to about 100° C.

3. The method of claim 1, wherein the solvent b) is selected from acetonitrile, dichloroethane, toluene, chlorobenzene, xylene, acetic acid, acetic anhydride, propionic acid, butyric acid, and combinations thereof.

4. The method of claim 1, wherein the halogenation reagent is selected from a chlorination reagent, a bromination reagent, an iodination reagent, and combinations thereof.

5. The method of claim 1, wherein the method step ii) of reacting the first mixture occurs at a reaction temperature in the range of about 20° C. to about 140° C.

6. The method of claim 1, wherein the oxidation agent is selected from oxygen, chlorine, sodium hypochlorite, chromium trioxide, 3-chloroperoxybenzoic acid, hydrogen peroxide, peroxyacetic acid, potassium peroxymonosulfate, potassium permanganate, and combinations thereof.

7. The method of claim 1, wherein the catalyst is selected from sulfuric acid, hydrogen chloride, nitric acid, and combinations thereof.

8. The method of claim 1, wherein the method step iv) of reacting the further mixture occurs at a reaction temperature in the range of about 20° C. to about 100° C.

9. The method of claim 1, wherein the compound of Formula III is prepared according to a method comprising
I) forming a mixture comprising
A) a compound of Formula II, wherein

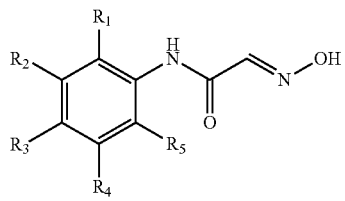

(Formula II)

each of $R_1$-$R_5$ is independently selected from hydrogen, halogen, and $C_1$-$C_5$ alkyl; and
wherein the compound of Formula II is prepared according to a method comprising
i) forming a mixture comprising
a) a compound of Formula I, wherein

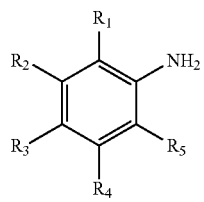

(Formula I)

each of $R_1$-$R_5$ is independently selected from hydrogen, halogen, and $C_1$-$C_5$ alkyl;
b) chloral hydrate;
c) a hydroxylamine derivative;
d) a solvent;
e) an inorganic salt; and
f) an acid; and
ii) reacting the mixture; and
B) an acid; and
II) reacting the mixture.

10. A method of preparing a compound of Formula VI, wherein

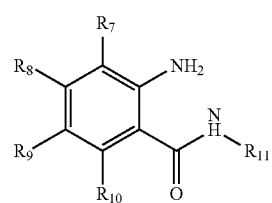

(Formula VI)

each of $R_7$-$R_{10}$ is independently selected from hydrogen, halogen, halogenated $C_1$-$C_5$ alkyl, and $C_1$-$C_5$ alkyl;
wherein at least one of $R_7$-$R_{10}$ is a halogen; and
wherein $R_{11}$ is selected from branched $C_1$-$C_{10}$ alkyl and unbranched $C_1$-$C_{10}$ alkyl, the method comprising
I) forming a mixture comprising
A) a compound of Formula V, wherein

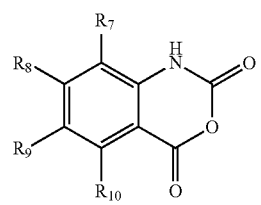

(Formula V)

each of $R_7$-$R_{10}$ is independently selected from hydrogen, halogen, halogenated $C_1$-$C_5$ alkyl, and $C_1$-$C_5$ alkyl;
wherein at least one of $R_7$-$R_{10}$ is a halogen; and
wherein the compound of Formula V is prepared according to a method comprising
i) forming a mixture comprising
a) a compound of Formula IV, wherein

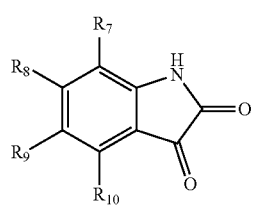

(Formula IV)

each of $R_7$-$R_{10}$ is independently selected from hydrogen, halogen, halogenated $C_1$-$C_5$ alkyl, and $C_1$-$C_5$ alkyl; and
wherein at least one of $R_7$-$R_{10}$ is a halogen;
b) an oxidation agent;
c) a solvent; and
d) a catalyst; and
ii) reacting the mixture;
B) an alkylamine; and
C) a solvent; and
II) reacting the mixture.

11. The method of claim 10, wherein the alkylamine comprises a functional group selected from branched $C_1$-$C_{10}$ alkyl and unbranched $C_1$-$C_{10}$ alkyl.

12. The method of claim 10, wherein the solvent C) is selected from acetonitrile, dichloroethane, toluene, chlorobenzene, xylene, methanol, ethanol, isopropanol, ethyl acetate, isopropyl acetate, and combinations thereof.

13. The method of claim 10, wherein the method step II) of reacting the mixture occurs at a reaction temperature in the range of about 0° C. to about 100° C.

14. The method of claim 10, wherein the oxidation agent is selected from oxygen, chlorine, sodium hypochlorite, chromium trioxide, 3-chloroperoxybenzoic acid, hydrogen peroxide, peroxyacetic acid, potassium peroxymonosulfate, potassium permanganate, and combinations thereof.

15. The method of claim 10, wherein the catalyst is selected from sulfuric acid, hydrogen chloride, nitric acid, and combinations thereof.

16. The method of claim 1, wherein step iii) comprises introducing a second mixture to the first mixture to form the further mixture, the second mixture comprising d) the oxidation agent and e) the catalyst.

17. The method of claim 1, wherein the method to prepare the compound of Formula V is a single-pot method.

* * * * *